US012788340B2

(12) United States Patent
Zhan et al.

(10) Patent No.: US 12,788,340 B2
(45) Date of Patent: Nov. 10, 2026

(54) METHOD AND APPARATUS FOR OBJECT SCAN DATA CORRECTION IN A PHOTON COUNTING X-RAY IMAGING SYSTEM WITH AUTOMATIC EXPOSURE CONTROL

(71) Applicant: Canon Kabushiki Kaisha, Tokyo (JP)

(72) Inventors: Xiaohui Zhan, Vernon Hills, IL (US); Ruoqiao Zhang, Vernon Hills, IL (US); Thomas Labno, Vernon Hills, IL (US)

(73) Assignee: Canon Kabushiki Kaisha, Tokyo (JP)

( * ) Notice: Subject to any disclaimer, the term of this patent is extended or adjusted under 35 U.S.C. 154(b) by 189 days.

(21) Appl. No.: 18/919,544

(22) Filed: Oct. 18, 2024

(65) Prior Publication Data

US 2026/0108222 A1 Apr. 23, 2026

(51) Int. Cl.
*A61B 6/42* (2024.01)
*A61B 6/00* (2024.01)
*A61B 6/58* (2024.01)

(52) U.S. Cl.
CPC ............ *A61B 6/4241* (2013.01); *A61B 6/542* (2013.01); *A61B 6/582* (2013.01)

(58) Field of Classification Search
CPC .................................................... A61B 6/4241
See application file for complete search history.

(56) References Cited

U.S. PATENT DOCUMENTS 11,249,035 B2 2/2022 Zhan et al.
11,653,892 B2 5/2023 Zhan et al.
11,944,484 B2 4/2024 Zhan et al.
2004/0190679 A1* 9/2004 Waggener ............ A61B 6/4035 378/54
2012/0093282 A1* 4/2012 Kappler ................. A61B 6/032 378/18
2012/0201344 A1* 8/2012 Feuerlein ............... A61B 6/032 378/4
2013/0301799 A1 11/2013 Kang et al.
2018/0078233 A1* 3/2018 Jin ......................... A61B 6/032
2022/0342098 A1 10/2022 Zhan et al.
2023/0389883 A1* 12/2023 Fan ........................ A61B 6/405

* cited by examiner

*Primary Examiner* — Edwin C Gunberg
(74) *Attorney, Agent, or Firm* — Oblon, McClelland, Maier & Neustadt, L.L.P.

(57) ABSTRACT

A method for performing object scan data correction in an X-ray imaging system having a photon-counting detector is provided. The method includes acquiring calibration scan data from a calibration scan performed using a plurality of slabs, performing function fitting based on the acquired calibration scan data to generate a plurality of fitting functions corresponding to the plurality of slabs, each corresponding fitting function representing a relationship between a counting measurement detected with respect to one slab of the plurality of slabs and a tube current applied to the X-ray tube, establishing a calibration table based on the acquired calibration scan data, acquiring object scan data from an object scan performed on an imaging object, performing data correction for the acquired object scan data, based on the established calibration table and the generated plurality of fitting functions and reconstructing an image of the imaging object based on the performed data correction.

20 Claims, 15 Drawing Sheets

METHOD AND APPARATUS FOR OBJECT SCAN DATA CORRECTION IN A PHOTON COUNTING X-RAY IMAGING SYSTEM WITH AUTOMATIC EXPOSURE CONTROL

CROSS-REFERENCE TO RELATED APPLICATIONS

This application is related to U.S. Pat. No. 11,249,035 entitled "TWO-STEP MATERIAL DECOMPOSITION CALIBRATION METHOD FOR A FULL SIZE PHOTON COUNTING COMPUTED TOMOGRAPHY SYSTEM," filed on Jun. 29, 2020 and granted on Feb. 15, 2022; U.S. Pat. No. 11,653,892 entitled "COUNTING RESPONSE AND BEAM HARDENING CALIBRATION METHOD FOR A FULL SIZE PHOTON-COUNTING CT SYSTEM," filed on Jan. 22, 2021 and granted on May 23, 2023; and U.S. Pat. No. 11,944,484 entitled "MATERIAL DECOMPOSITION CALIBRATION METHOD AND APPARATUS FOR A FULL SIZE PHOTON COUNTING CT SYSTEM," filed on Mar. 31, 2021 and granted on Apr. 2, 2024. The contents of the above-identified patents are incorporated herein by reference.

BACKGROUND

Field

The disclosure relates to X-ray Computed Tomography (CT) imaging technology based on a photon counting detector.

Description of the Related Art

Computed tomography (CT) imaging has been commonly used for medical diagnosis. Generally, a radiation source, such as an X-ray tube, irradiates a patient's body at a series of projection angles and projection images are generated from various perspectives. Images of the patient's body can be reconstructed from these projection images.

However, ionizing radiation from CT scans can increase the risk of developing cancer later in life. It has been reported that CT scanning contributes the highest collective amount of medical radiation exposure in the United States compared with any other medical imaging modality.

Typically, different diagnostic CT imaging protocols require varying exposure levels for different body anatomies. It is ideal to scan patients with the lowest possible radiation dose that still produces clinically acceptable image quality. However, reducing the dose often leads to a low signal-to-noise ratio (SNR), which can impact the detectability of certain structures or pathologies.

To address this problem, one effective approach in CT imaging is the modulation of X-ray tube current, known as automatic exposure control (AEC). AEC aims to optimize CT scan exposures automatically by reducing radiation dose to the patient's body while maintaining consistent image quality, thus simplifying the radiologist's workflow. This approach has found widespread application across various protocols and anatomical regions in CT scanners, including CTs based on photon counting detectors (PCDs).

Due to the asymmetrical shape of most patient anatomy, the X-ray tube current can be modulated in the X-Y plane during one rotation and along the Z-axis. This modulation considers varying attenuation pathlengths to achieve a more uniform dose at the detector plane throughout the scan, thereby optimizing the balance between image quality and patient dose efficiency. However, calibration of the forward model of the PCD detector typically uses data samples acquired under discrete tube currents, posing a challenge for the calibration or correction of PCD-based CT scanners with an AEC design.

Therefore, it is desirable to develop an improved calibration or correction approach for PCD CT scanners equipped with AEC modulation.

SUMMARY

The present disclosure relates to a method for performing object scan data correction in an X-ray imaging system having a photon-counting detector. The X-ray imaging system includes an X-ray tube for emitting X-rays. The method includes acquiring calibration scan data from a calibration scan performed using a plurality of slabs, performing function fitting based on the acquired calibration scan data to generate a plurality of fitting functions corresponding to the plurality of slabs, each corresponding fitting function representing a relationship between a counting measurement detected with respect to one slab of the plurality of slabs and a tube current applied to the X-ray tube, establishing a calibration table based on the acquired calibration scan data, acquiring object scan data from an object scan performed on an imaging object, performing data correction for the acquired object scan data, based on the established calibration table and the generated plurality of fitting functions and reconstructing an image of the imaging object based on the performed data correction.

The disclosure additionally relates to an apparatus for performing object scan data correction in an X-ray imaging system having a photon-counting detector. The X-ray imaging system includes an X-ray tube for emitting X-rays. The apparatus includes processing circuitry configured to acquire calibration scan data from a calibration scan performed using a plurality of slabs, perform function fitting based on the acquired calibration scan data to generate a plurality of fitting functions corresponding to the plurality of slabs, each corresponding fitting function representing a relationship between a counting measurement detected with respect to one slab of the plurality of slabs and a tube current applied to the X-ray tube, establish a calibration table based on the acquired calibration scan data, acquire object scan data from an object scan performed on an imaging object, perform data correction for the acquired object scan data, based on the established calibration table and the generated plurality of fitting functions, and reconstruct an image of the imaging object based on the performed data correction.

The disclosure additionally relates to a method for performing object scan data correction in an X-ray imaging system having a photon-counting detector. The X-ray imaging system includes an X-ray tube for emitting X-rays. The method includes acquiring calibration scan data from a calibration scan performed using each slab of a plurality of slabs, with a first number ($n_1$) of tube currents applied to the X-ray tube, establishing, based on the acquired calibration scan data, the first number ($n_1$) of calibration tables to be used in data correction, each calibration table of the first number ($n_1$) of calibration tables corresponding to one tube current of the first number ($n_1$) of tube currents, calculating, for a second number ($n_2$) of tube currents, the second number ($n_2$) of calibration tables based on the first number ($n_1$) of calibration tables, where the second number ($n_2$) of tube currents are different from the first number ($n_1$) of tube currents, acquiring object scan data from an object scan performed on an imaging object, performing the data correction for the acquired object scan data, based on the first number ($n_1$) and second number ($n_2$) of calibration tables, and reconstructing an image of the imaging object based on the performed data correction.

Note that this summary section does not specify every embodiment and/or incrementally novel aspect of the present disclosure or claimed invention. Instead, the summary only provides a preliminary discussion of different embodiments and corresponding points of novelty. For additional details and/or possible perspectives of the disclosure and embodiments, the reader is directed to the Detailed Description section and corresponding figures of the present disclosure as further discussed below.

BRIEF DESCRIPTION OF THE DRAWINGS

The application will be better understood in light of the description, which is given in a non-limiting manner, accompanied by the attached drawings in which.

DETAILED DESCRIPTION OF THE PREFERRED EMBODIMENTS

Figure 1:
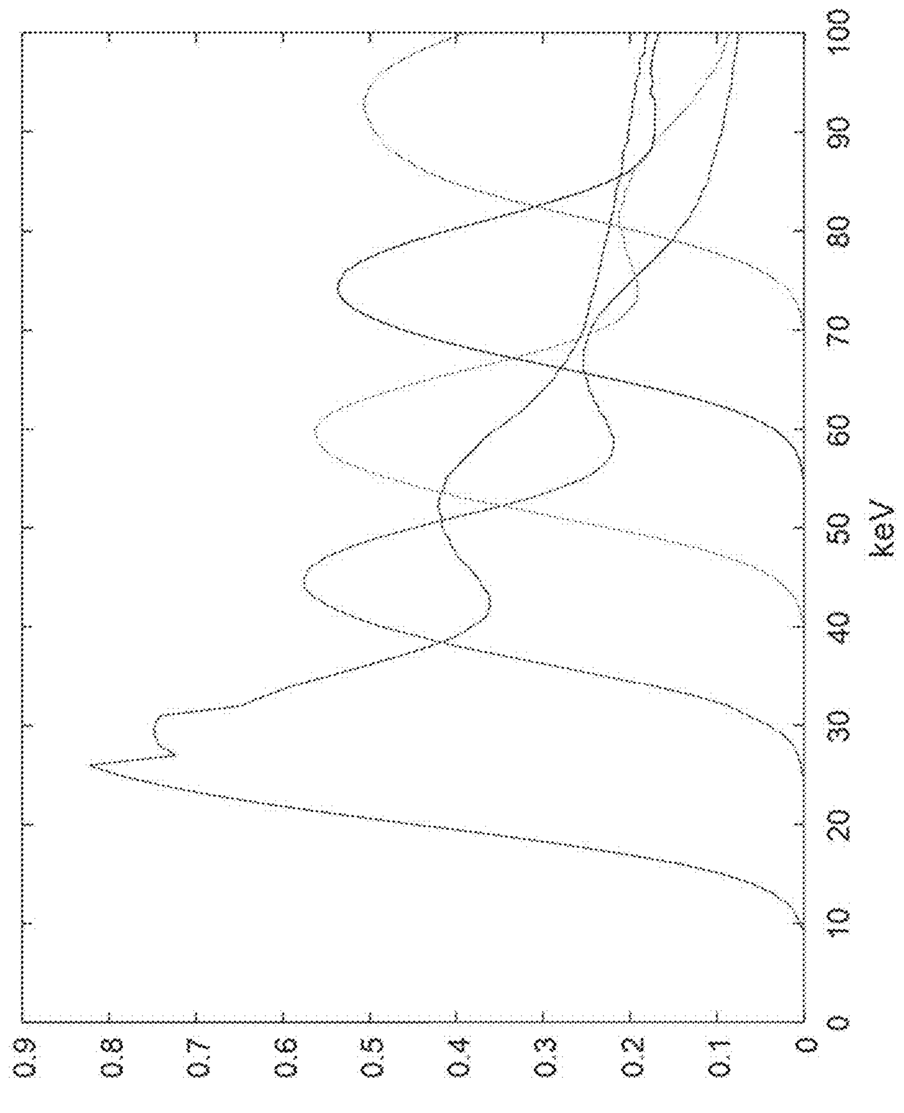
FIG. 1 shows an example of a bin response function $S_b(E)$ for a photon-counting detector, with each curve standing for an exemplary function for an energy bin.

The following disclosure provides many different embodiments, or examples, for implementing different features of the provided subject matter. Specific examples of components and arrangements are described below to simplify the present disclosure. These are, of course, merely examples and are not intended to be limiting.

For example, the order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present disclosure can be embodied and viewed in many different ways.

Furthermore, as used herein, the words "a," "an," and the like generally carry a meaning of "one or more," unless stated otherwise.

Conventionally, energy-integrating detectors (EIDs) and photon-counting detectors (PCDs) have been used to measure Computed Tomography (CT) projection data. PCDs offer many advantages including their capacity for performing spectral CT, wherein the PCDs resolve the counts of incident X-rays into spectral components referred to as energy bins, such that collectively the energy bins span the energy spectrum of the X-ray beam. Unlike a non-spectral CT, a spectral CT generates information due to different materials exhibiting different X-ray attenuation as a function of the X-ray energy. These differences enable a decomposition of the spectrally resolved projection data into different material components, for example, the two material components of the material decomposition can be bone and water.

Even though PCDs have fast response times, at high X-ray flux rates indicative of clinical X-ray imaging, multiple X-ray detection events on a single detector can occur within the detector's time response, a phenomenon called pileup. Left uncorrected, pileup effects distort the PCD energy response and can degrade reconstructed images from PCDs. When these effects are corrected, the spectral CT has many advantages over conventional CT. Various clinical applications can benefit from spectral CT technology, including improved material differentiation since spectral CT extracts complete tissue characterization information from the scanned object.

One challenge for more effectively using semiconductor-based PCDs for spectral CT is performing the material decomposition of the projection data in a robust and efficient manner. For example, correction of pileup in the detection process can be imperfect, and these imperfections degrade the material components resulting from the material decomposition.

As mentioned above, in a photon-counting CT system, the semiconductor-based detector using direct conversion is designed to resolve the energy of the individual incoming photons and measure multiple energy bin counts for each integration period. However, due to the detection physics in such semiconductor materials (e.g., CdTe/CZT), the detector energy response is largely degraded/distorted by charge sharing, k-escape, and scattering effects in the energy deposition and charge induction process, as well as electronic noise in the associated front-end electronics. Due to finite signal induction time, at high count-rate conditions, pulse pile-up also distorts the energy response, as discussed above.

Due to the non-uniformity in sensor materials and the complexity of the integrated detection system, it is difficult to accurately model detector responses for a PCD based solely on physics theories or Monte Carlo simulations with certain modeling of the signal induction process, which determines the accuracy of the forward model of each measurement. Moreover, uncertainties in modeling the incident X-ray tube spectrum further introduce additional errors in the forward model. All these factors eventually degrade the accuracy of the attenuation line-integral (for a counting imaging mode) or material decomposition accuracy (for a spectral imaging mode) derived from PCD measurements, consequently affecting the quality of generated spectral images.

FIG. 1 shows an example of the bin response function of a photon-counting detector. As depicted in the figure, due to charge sharing, pulse pileup effects, etc., the bin response function has a very broad distribution beyond the ideal bin energy window for each counter.

As mentioned above, U.S. Pat. Nos. 11,249,035, 11,653,892, and 11,944,484 propose PCD forward models and calibration methods for both counting and spectral imaging modes. Typically, a calibration procedure can be applied based on multiple transmission measurements of various known attenuation pathlengths to refine the forward model, such that it aligns with calibration measurements. These approaches normally use static scans with materials of predetermined thicknesses, often in rectangular slab shapes.

For example, when the number of the energy bins is n, the PCD forward model can be given by Equation (1):

$$N_{b,j}(b=1,\ \ldots\ ,n) = \int_{T_b}^{T_{b+1}} \Phi_b(E') \int_{E_{min}}^{E_{max}} N_{0,j} S_{0,j}(E) D(E,\ E') e^{\sum_{k=1}^{K} \mu_k(E) l_k} dE dE' \quad (1)$$

where E denotes the incident energy, E' denotes the measured energy, $N_{b,j}$ denotes the counts measured at a given detector pixel j for an energy bin b, $\Phi_b(E')$ denotes the binning function which models the function of the data acquisition system (DAS) (or ASIC) that generates digital data indicating counts detected by the detector, $$\Phi_b(E') = \begin{cases} 1, & T_b \leq E' \leq T_{b+1} \\ 0, & \text{others} \end{cases},$$

$T_b$ and $T_{b+1}$ are the low and high energy thresholds of the energy bin b, $E_{min}$ and $E_{max}$ are the low and high energy thresholds of the incident spectrum energy range, $N_{0,j}$ is the incident beam spectrum, which can be represented by the air flux measured at the detector pixel j using an air scan, $S_{0,j}(E)D(E, E')$ is the detector response calibration term ("DR"), and $$\sum_{k=1}^{K} \mu_k(E) l_k$$

is the attenuation sample at the detector pixel j.

As mentioned above, to calibrate the forward model parameters, a group of slab scans using known materials and thicknesses can be conducted. Let $N_{b,i,j}$ be the measured count at the detector pixel j for the energy bin b and a slab i (i=1, . . . , m), the parameters in the PCD forward model can be determined by solving the minimization problem using Equation (2):

$$DR_j^* = \text{argmin}_{DR} \sum_{b=1}^{n} \sum_{i=1}^{m} (y_{b,i}(DR_j) - N_{b,i,j})^2 \quad (2)$$

where $y_{b,i}$ is the counts calculated with respect to the energy bin b, the slab i, and the detector pixel j, with $DR_j$ under a certain air flux $N_{0,j}$ based on Equation (1).

Note that the above equations are provided for the spectral imaging mode of the photon-counting CT. When the photon-counting CT operates under the counting imaging mode, the calculation can be reduced as below:

$$DR_i^* = \text{argmin}_{DR} \sum_{i=1}^{m} (y_{tot,i}(DR_j) - N_{tot,i,j})^2 \quad (3)$$

where $$y_{tot,i} = \Sigma_{b=1}^{n} y_{b,i}, \text{ and } N_{tot,i,j} = \sum_{b=1}^{n} N_{b,i,j}.$$

Figure 2A:
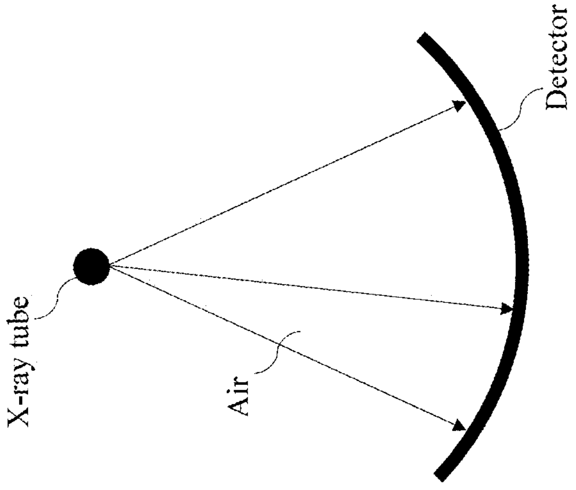
FIGS. 2A-2C show an air scan and slab scans performed during a calibration procedure, where the slab scans use different combinations of known materials and thicknesses.
Figure 2B:
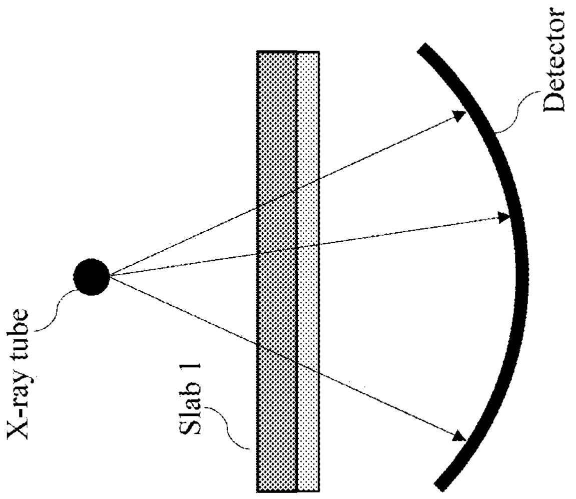
Figure 2C:
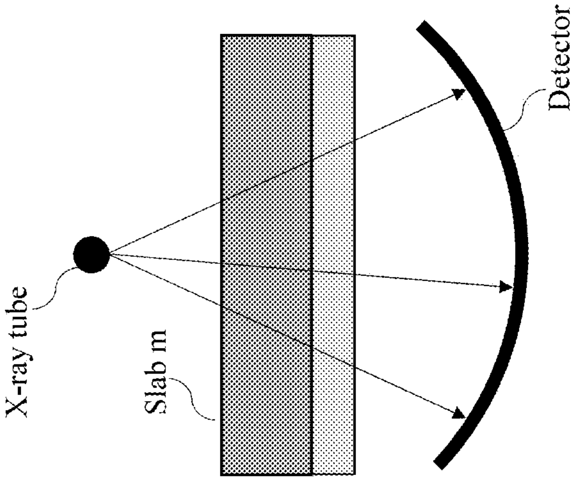

For example, when the PCD calibration scan data is acquired using slabs 1, . . . , m, the procedure generates a set of measurements with the attenuation samples $$att_i = \sum_{k=1}^{K} \mu_k l_k(i),$$

i=1, . . . , m. FIGS. 2A, 2B, and 2C show the air scan and slab scans using different combinations of known materials and thicknesses. In the example shown in FIGS. 2B-2C, the PCD calibration slab scans utilize two basis materials (i.e., K=2), such as solid water/aluminum, or other similar combinations (e.g., iodine, calcium, etc.), to cover an attenuation phase space that would be encountered in object scans. Each of these data points $N_{b,i,j}$ (for the spectral imaging mode; or $N_{tot,i,j}$, for the counting imaging mode) will be used for the cost function calculation.

Due to practical reasons, the calibration procedure is generally conducted at discrete tube currents. Then, the calibration data is used to generate calibration tables associated with these specific tube currents. When a subsequent object scan is performed on the imaging object with fixed tube currents identical to those used during the calibration procedure, sufficiently accurate calibration can be achieved based on these calibration tables.

However, it is difficult to yield the required accuracy by applying the calibration tables under uncalibrated flux conditions. For example, a calibration table associated with a lower tube current cannot be directly used to calibrate object scan data acquired at higher tube currents, due to the increased pileup effect in the measurements.

Moreover, compared with conventional EID CTs, PCD CTs typically have smaller pixel elements, leading to much bigger data sizes. Given the limited calibration time allowed for a CT imaging system at clinical sites, it remains a challenging task to keep the calibration table size manageable for object scan data processing and reconstruction.

The present disclosure provides a method and apparatus that enable accurate calibration or correction in photon counting CTs with AEC modulation, even when the calibration scans are conducted at discrete tube current points. This method and apparatus can be applied in the context of the PCD forward model and calibration method as described in U.S. Pat. Nos. 11,249,035, 11,653,892, and 11,944,484. However, the method and apparatus are also applicable to any PCD calibration or correction scheme that uses calibration data acquired at discrete tube current points. The CT imaging systems are not limited to CZT/CdTe PCDs, but can also use other semiconductor materials that experience similar issue in terms of detector response uniformity across pixels and the pileup effect, which distorts the response under different flux conditions.

Figure 3:
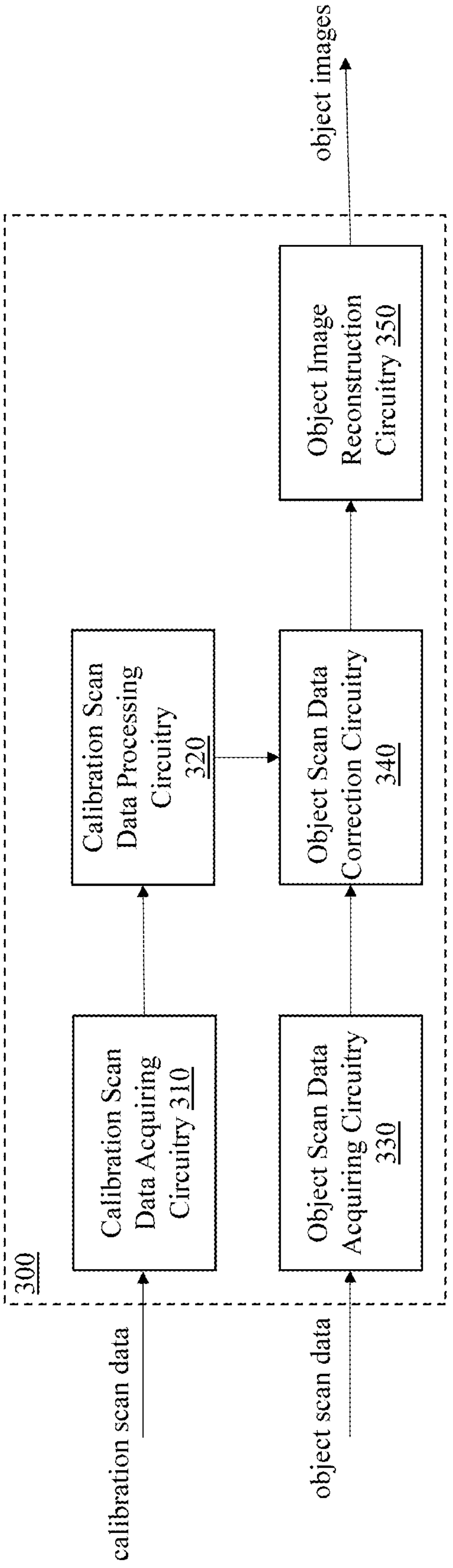
FIG. 3 shows a block diagram of an object scan data correction apparatus 300 according to embodiments of the disclosure.

FIG. 3 shows a block diagram of an object scan data correction apparatus 300 according to embodiments of the disclosure. The object scan data correction apparatus 300 includes calibration scan data acquiring circuitry 310, calibration scan data processing circuitry 320, object scan data acquiring circuitry 330, object scan data correction circuitry 340, and object image reconstruction circuitry 350.

The calibration scan data acquiring circuitry 310 acquires scan data generated from a calibration procedure and send it to the calibration scan data processing circuitry 320. As mentioned previously, the calibration procedure can include an air scan and multiple slab scans conducted on slabs of different attenuation pathlengths, with discrete tube currents applied to the X-ray tube. The calibration scan data processing circuitry 320 processes the received data to generates a set of calibration tables associated with those discrete tube currents applied during the calibration procedure, as well as a set of fitting functions associated with the slabs.

For example, in one embodiment, the fitting functions generated based on the calibration scan data can be used to process the object scan data, as if the object scan data were acquired with the tube currents used during the calibration procedure are applied. In another embodiment, supplemental calibration data can be calculated based on the fitting functions, while the object scan data can be kept unchanged. An alternative embodiment can include calculating supplemental calibration tables based on the calibration tables generated using the calibration scan data, and both the supplemental calibration tables and the generated calibration tables can then be used in correction of the object scan data.

The object scan data acquiring circuitry 330 acquires scan data generated from an object scan performed on an imaging object and sends it to the object scan data correction circuitry 340. The object scan data correction circuitry 340 performs data correction for the object scan data, based on the calibration tables and the fitting functions. The object image reconstruction circuitry 350 then reconstructs an image of the imaging object based on this data correction.

Figure 4:
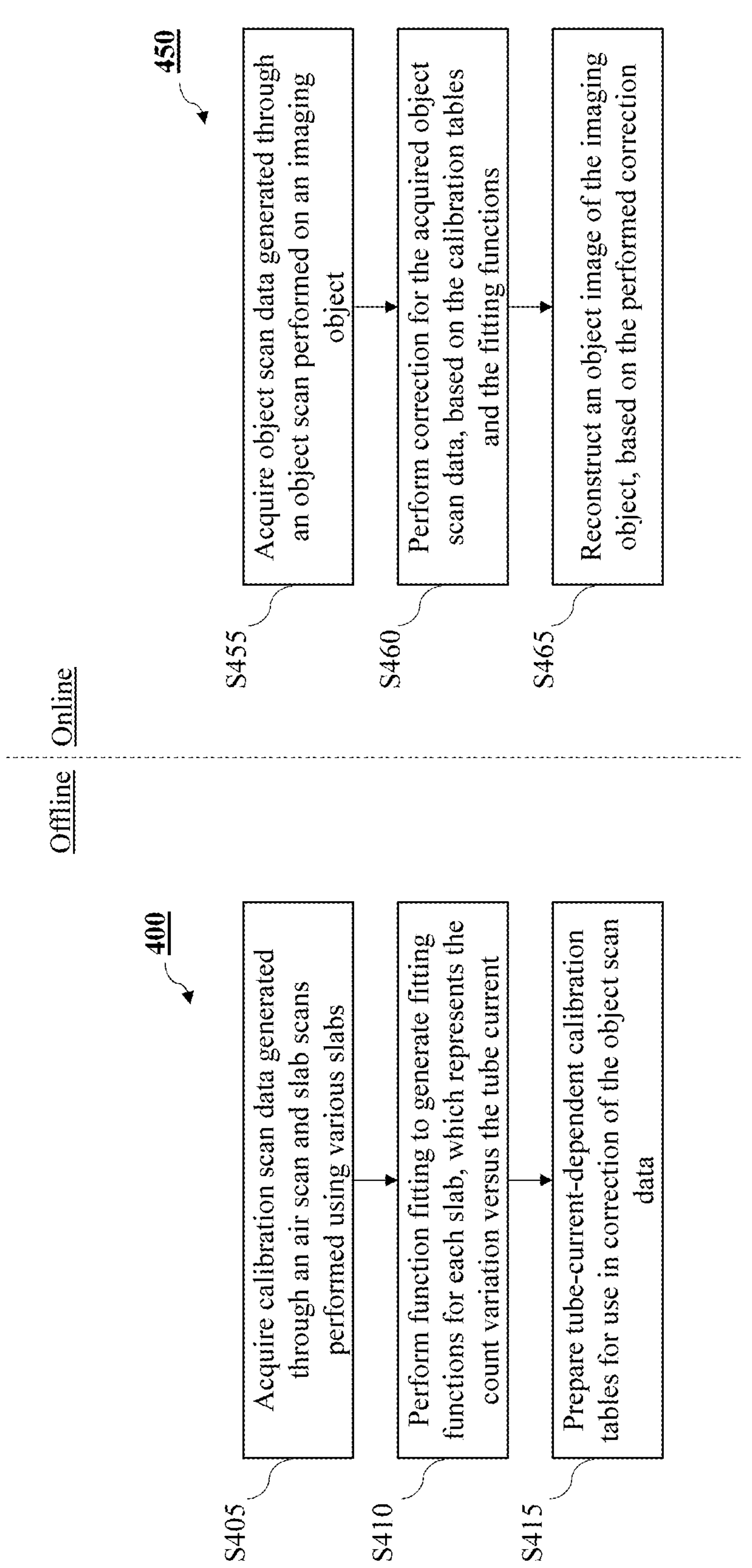
FIG. 4 shows a flow chart of an object scan data correction process including an offline portion 400 and an online portion 450, according to embodiments of the disclosure.

FIG. 4 shows a flow chart of an object scan data correction process according to embodiments of the disclosure. The object scan data correction process includes an offline portion 400 performed on the calibration scan data and an online portion 450 performed on the object scan data.

The offline portion 400 starts at step S405 by acquiring the calibration scan data generated through the calibration procedure including the air scan and slab scans. In step S410, function fitting is performed to generate fitting functions corresponding to the slabs, based on the calibration scan data. In step S415, calibration tables are established based on the calibration scan data, for use in correction of the object scan data.

The online portion 450 starts at step S455 by acquiring the object scan data generated through the object scan performed on the imaging object. In step S460, based on the calibration tables and the fitting functions, data correction is conducted for the acquired object scan data. In step S465, an object image of the imaging object is reconstructed based on the data correction.

The processing on the calibration scan data and the correction on the objection scan data will be described below with reference to different embodiments of this disclosure.

Figure 5:
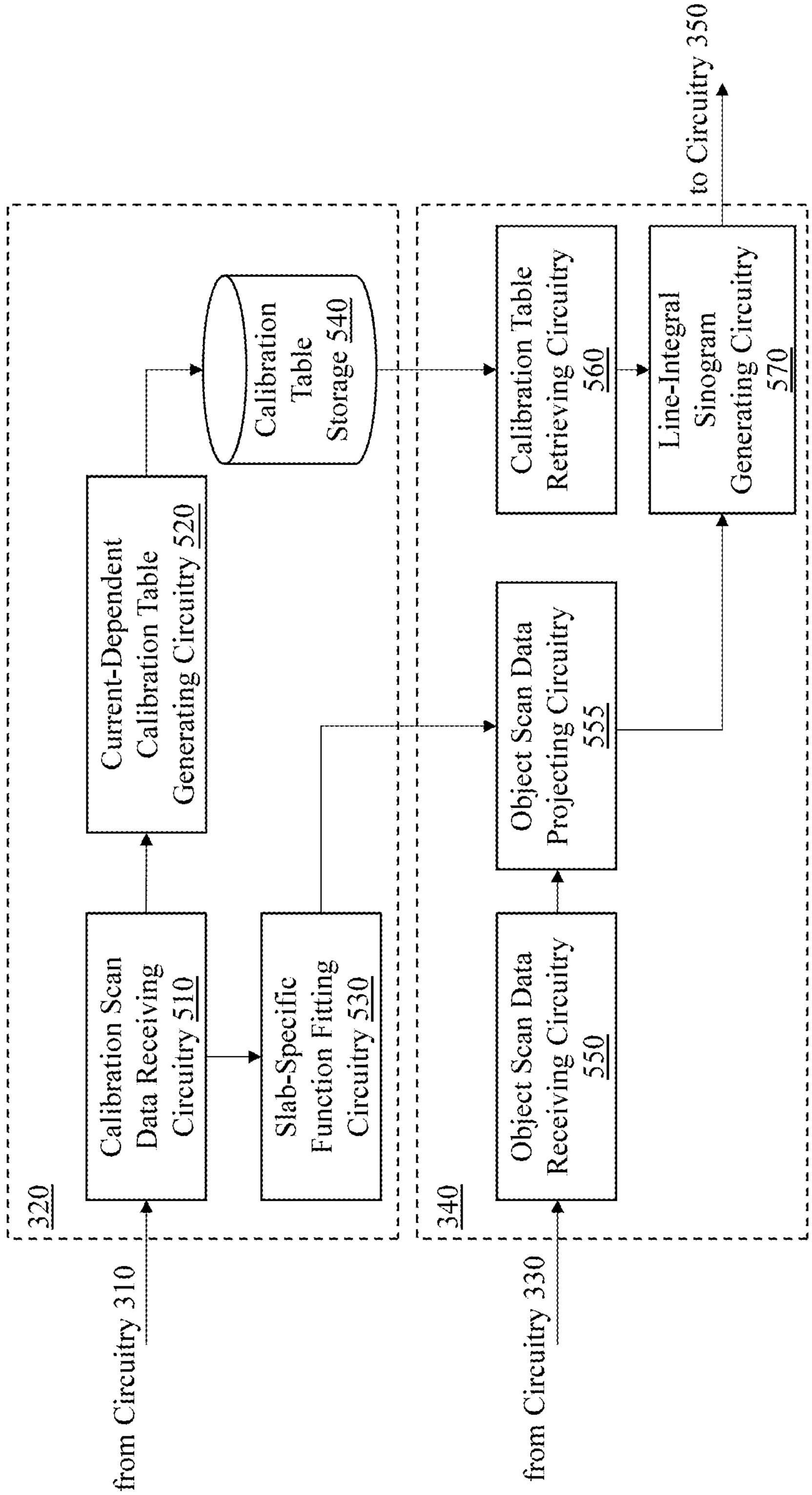
FIG. 5 shows a block diagram of calibration scan data processing circuitry 320 and object scan data correction circuitry 340 according to embodiments of the disclosure.

FIG. 5 shows a block diagram of the calibration scan data processing circuitry 320 and the object scan data correction circuitry 340 according to one embodiment of the disclosure. The calibration scan data processing circuitry 320 includes calibration scan data receiving circuitry 510, current-dependent calibration table generating circuitry 520, slab-specific function fitting circuitry 530, and calibration table storage 540. The object scan data correction circuitry 340 includes object scan data receiving circuitry 550, object scan data projecting circuitry 555, calibration table retrieving circuitry 560, and line-integral sinogram generating circuitry 570.

The calibration scan data receiving circuitry 510 receives calibration scan data from the calibration scan data acquiring circuitry 310, and sends the received data to the current-dependent calibration table generating circuitry 520 and the slab-specific function fitting circuitry 530. The current-dependent calibration table generating circuitry 520 generates calibration tables based on the calibration scan data, and stores the calibration tables in the calibration table storage 540.

As discussed previously, modeling the detector response in an EID CT is straightforward because it is uniform to the incident flux. However, due to the pulse pileup effect, the detector response in a PCD CT is sensitive to the incident flux, and thus sensitive to the tube current. To calibrate such effect and other distortions, it is necessary to calibrate the parameters of the detector response forward model using different slab measurements $N_i(m,j)$ at individual tube currents, where i is the energy bin index, m is the slab index, and j is the tube current index. Subsequently, a group of forward model calibration tables can be generated based on the known pathlengths of the used slabs and the measured bin counts.

Moreover, reference normalization can be applied to the slab scan data. For example, a reference detector can be installed at the X-ray tube side to detect the tube output flux. The readout value from the reference detector is proportional to the incident flux on the main pixel array of the PCD detector. Thus, the PCD output bin counts can first be normalized by the reference detector reading before subsequent data processing as follows:

$$N_i^{ref}(m, j) = N_b(m, j)/D_{ref} \tag{4}$$

where $D_{ref}$ is the value from the tube-side reference detector. Note that this reference normalization can be applied to not only the calibration scan data, but also the object scan data. For simplicity, in the following description, all measured counts refer to counts derived after this reference normalization, unless described otherwise.

Figure 6:
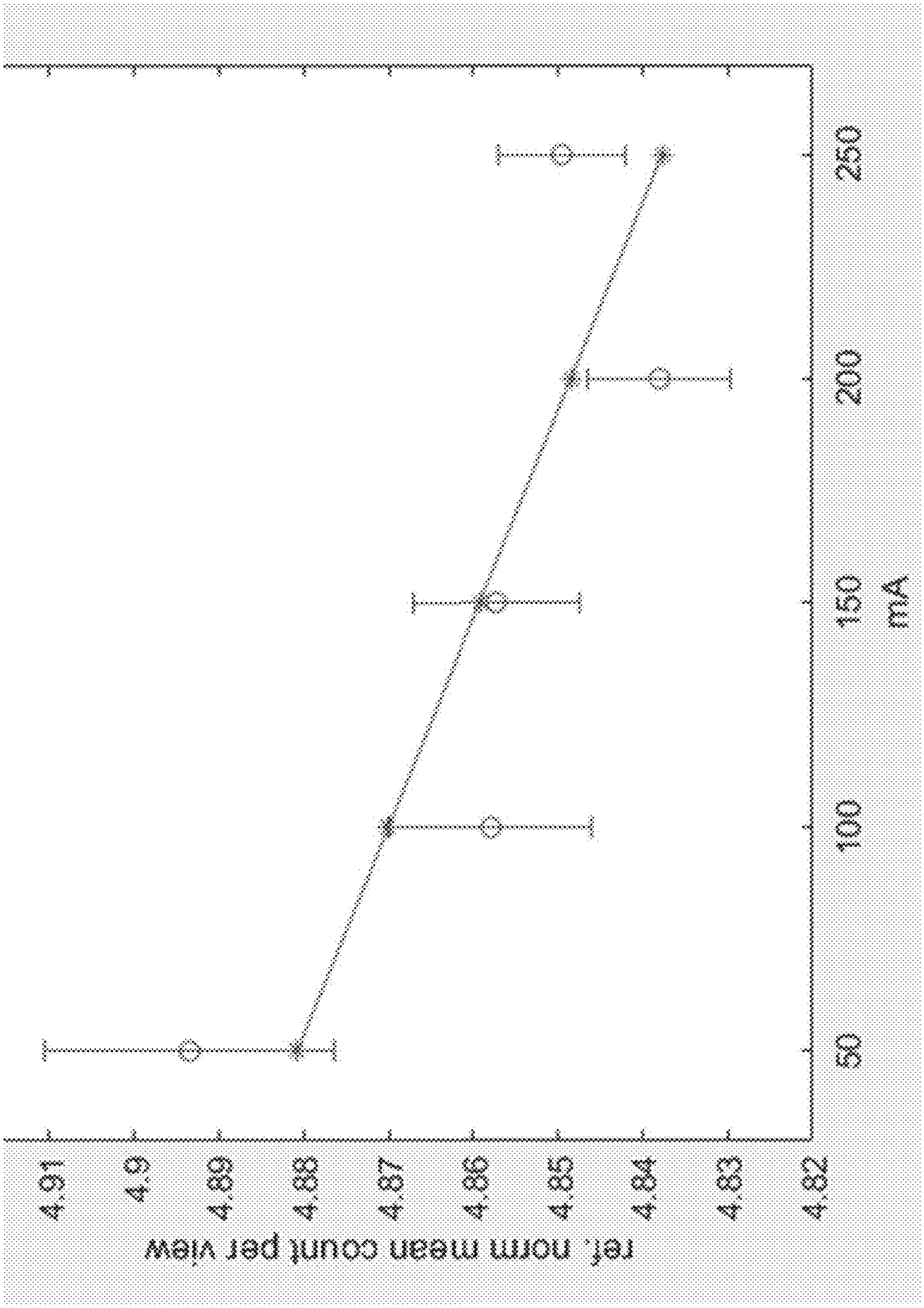
FIG. 6 shows exemplary function fitting of slab counting measurements along the tube current axis, according to embodiments of the disclosure.

Based on the behavior of the slab scan data at different tube currents, the slab-specific function fitting circuitry 530 determines a fitting function that maps the relationship between the counting measurements and the applied tube currents. FIG. 6 shows an exemplary linear fitting function for the reference normalized counting measurements of a selected slab, at a selected detector pixel, across a range of tube currents. As seen in FIG. 6, the fitted counts closely match the measured counts within the statistical error bars.

Figure 7:
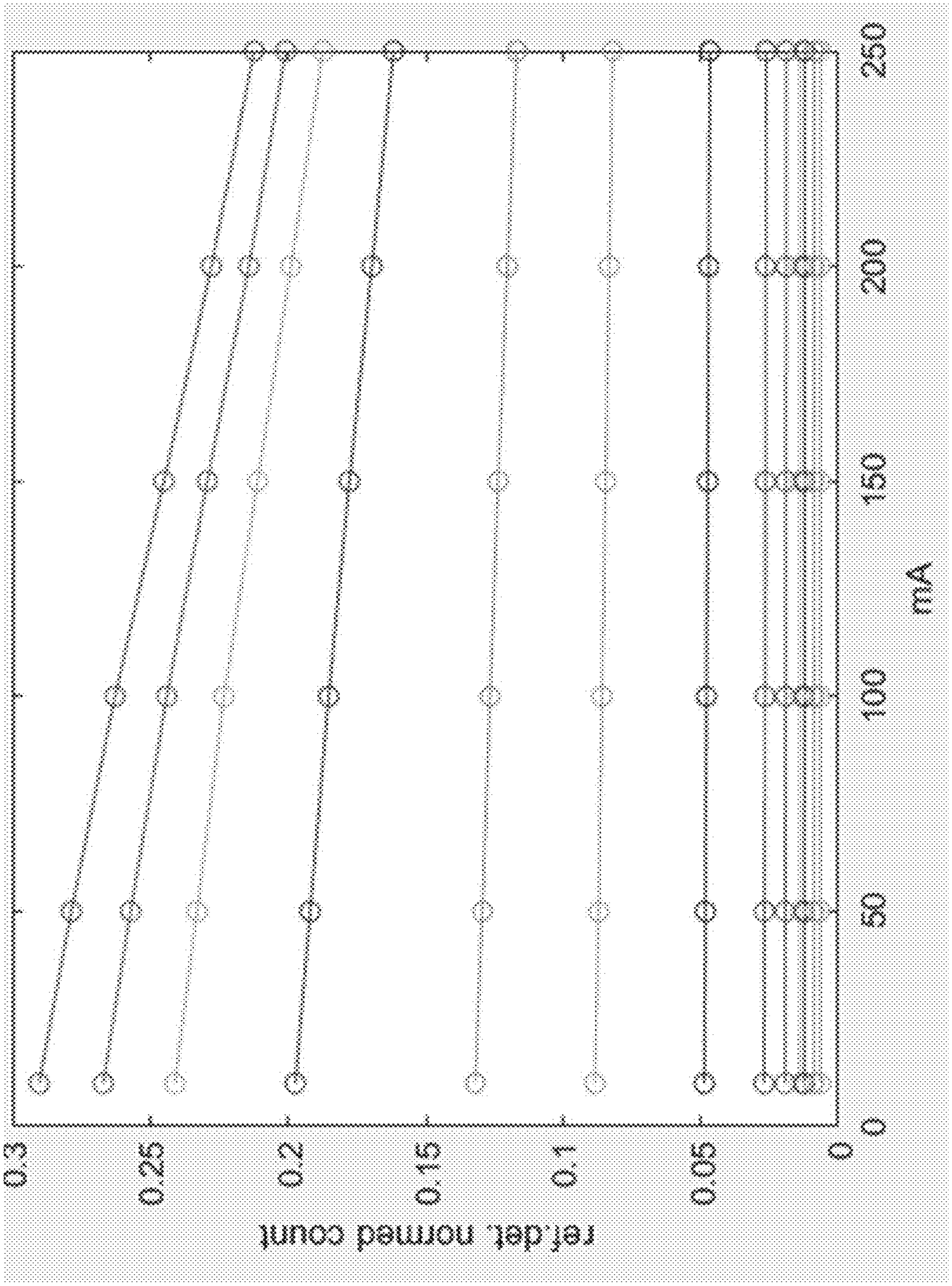
FIG. 7 shows exemplary fitting functions at a selected detector pixel according to embodiments of the disclosure, where each fitting function represents the relationship between counting measurements acquired from a corresponding slab and tube currents applied to the X-ray tube.

FIG. 7 shows exemplary fitting functions for multiple slabs at a selected detector pixel according to embodiments of the disclosure. Each fitting function represents the relationship between counting measurements acquired from a corresponding slab and the tube currents applied to the X-ray tube. In FIG. 7, the curves from top to bottom presents fitting functions generated for slabs ranging from thin to thick. For thinner slabs, the reference normalized counts decrease as the tube currents increase, due to the pulse pileup effect. For thicker slabs, the changes across the tube current range becomes smaller. This is because the count rates decrease quickly in thick slabs, resulting in a much smaller pileup effect.

By considering the statistical errors in the measurements, the parameters of the fitting functions can be estimated using the weighted least square approach, for example. Depending on the number of the tube currents applied in the calibration scan, different orders (k) of polynomial can be chosen as the fitting function, with k−1 being less than the total number of the calibration tube current points to prevent overfitting.

Let x represent the tube current value in mA, m be the slab index, a={a} the tunable parameters, $$N_i^{mean}(m, j)$$

the measured view-averaged counts at each tube current points, and $N_i(m,x)$ the calculated counts for slab m at the tube current x. The fitting function can be expressed as:

$$N_i(m, x) = f_i(a_{1,\ldots,k}, x) = a_0 + a_1x + a_2x^2 + \ldots\ a_kx^k \quad (5)$$

The parameters {a} can be determined by minimizing the following expression:

$$\{a\} = \text{argmin}\left(\sum (N_i(m, x_i) - N_i^{mean}(m, j))^2 / \sigma^2_{N_i(m,j)}\right) \quad (6)$$

Once the parameters {a} are determined, the fitting functions can be used by the object scan data projecting circuitry 555 for two-dimensional data projection, as described below.

The object scan data receiving circuitry 550 receives the object scan data from the object scan data acquiring circuitry 330, and send it to the object scan data projecting circuitry 555. Based on the fitting functions, the object scan data projecting circuitry 555 projects the counting measurement at each pixel of the PCD detector to a projected counting measurement, for each view of the object scan data.

As an example, in a scenario where the slab scans are performed at four fixed tube currents, 50 mA, 100 mA, 150 mA, and 200 mA, the current-dependent calibration table generating circuitry 520 generates calibration tables for these discrete tube current points. However, in a subsequent object scan with AEC design, the tube current can be modulated view by view automatically over a continuous range, based on the attenuation pathlength of the imaging object. For instance, some views of the object scan data might be acquired at a tube current of 60 mA, 70 mA, and so on. Directly applying the calibration tables for 50 mA, 100 mA, 150 mA, and 200 mA would not yield the required accuracy for calibrating these views.

Figure 8:
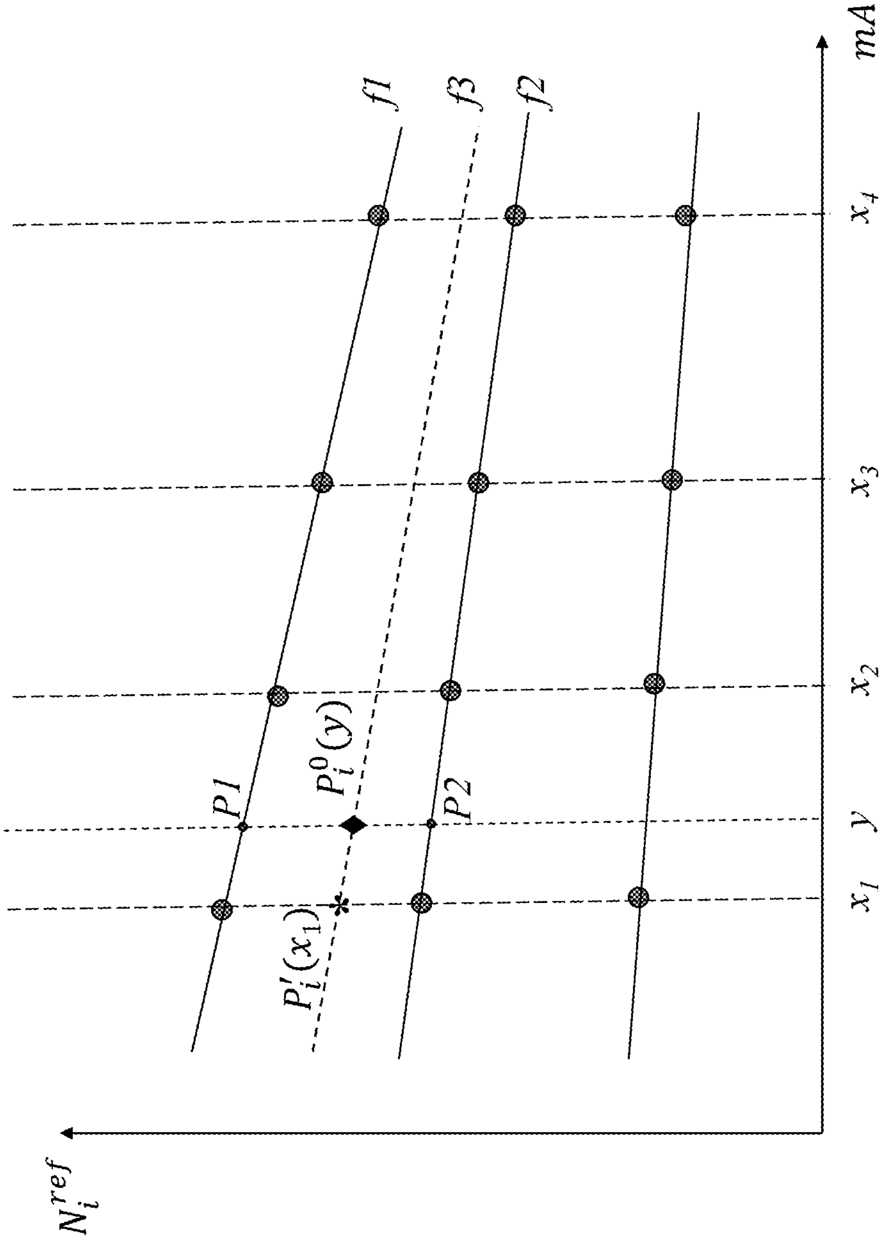
FIG. 8 illustrates a two-dimensional projection for projecting a detected counting measurement to a projected counting measurement at the closest calibration tube current, according to embodiments of the disclosure.

In this embodiment, the counting measurements obtained from the object scan with AEC modulation can be converted to counting measurements at the closest calibration tube currents, based on the fitting functions. FIG. 8 shows a counting measurement $$P_i^0(y)$$

(denoted by the symbol "♦") obtained from the object scan at a tube current y, which is different from any of the tube currents $x_1$ through $x_4$ applied during the calibration scan. Using the fitting functions as determined by Equation (5), a counting measurement $$P_i'(x_1)$$

(denoted by the symbol "*") at the nearest calibration tube current, $x_1$, can be calculated, as if the data acquisition were done at that calibration tube current.

Given that the measurements obtained from the object scan with AEC modulation are the tube current y and the counting measurement $$P_i^0(y),$$

a two-dimensional projection can be carried out in both the tube current dimension and the reference normalized count dimension.

Firstly, based on $$P_i^0(y),$$

the nearest fitting functions $f_1$ and $f_2$ can be determined from the fitting functions corresponding to the slabs. Two counting measurements $P_1$ and $P_2$ at the tube current y can be obtained as follows:

$$P_1 = f_1(a_1, y) \quad (7)$$

$$P_2 = f_2(a_2, y) \quad (8)$$

A fitting function $f_3$ corresponding to the attenuation pathlength of the view can be determined as a linear interpolation of the fitting functions $f_1$ and $f_2$:

$$f_3 = bf_1 + (1 - b)f_2 \quad (9)$$

-continued $$b = \frac{P_i^0(y) - P_2}{P_1 - P_2} \quad (10)$$

Using the determined fitting function $f_3$, the projected count $$P_i'(x_1)$$

at the nearest tube current $x_1$ can be calculated as follows:

$$P_i'(x_1) = f_3(x_1) \quad (11)$$

As a result, the detector calibration tables prepared for the tube current $x_1$ can be applied to this projected counting measurement $$P_i'(x_1)$$

to achieve accurate calibration.

The tube current y applied during the object scan can be directly measured from the X-ray tube in units of mA, or measured by the reference detector in any arbitrary unit proportional to the tube output flux.

To ensure the accuracy of the linear interpolation in Equations (9) and (10), the intervals between slab pathlengths should not be too large. The optimal interval design should balance calibration time and interpolation accuracy. In one embodiment, the slab pathlength interval is not larger than 5 cm, for example.

Besides the exemplary polynomial expressed by Equation (5), other types of fitting functions can be used, as long as they can fit the counting measurements with a reasonable number of parameters. The interpolation in Equation (9) is not limited to a linear method between two fitting functions; it can also use the nearest calibration point if the error is sufficiently small, or extend to more than two adjacent points with more complicated interpolation methods, such as cubic splines.

This two-dimensional interpolation can be applied for the object scan data in a pixel by pixel, view by view manner. For the counting imaging mode with AEC modulation, a total count $N_{tot}=\Sigma N_i$ is processed. For the spectral imaging mode with AEC modulation, individual energy bin counts $N_i$ are processed.

To optimize results in the object scan with AEC modulation, the fitting functions and interpolation methods can differ for the counting imaging mode and the spectral imaging mode, as well as for individual energy bins in the spectral imaging mode.

The object scan data projecting circuitry 555 sends the projected counting measurements to the line-integral sinogram generating circuitry 570. The calibration table retrieving circuitry 560 retrieves the calibration tables from the calibration table storage 540 and send them to the line-integral sinogram generating circuitry 570. The line-integral sinogram generating circuitry 570 uses the projected counting measurements to generate a line-integral sinogram, based on the retrieved calibration tables. The generated line-integral sinogram is sent to the object image reconstruction circuitry 350, for use in the image reconstruction.

Figure 9:
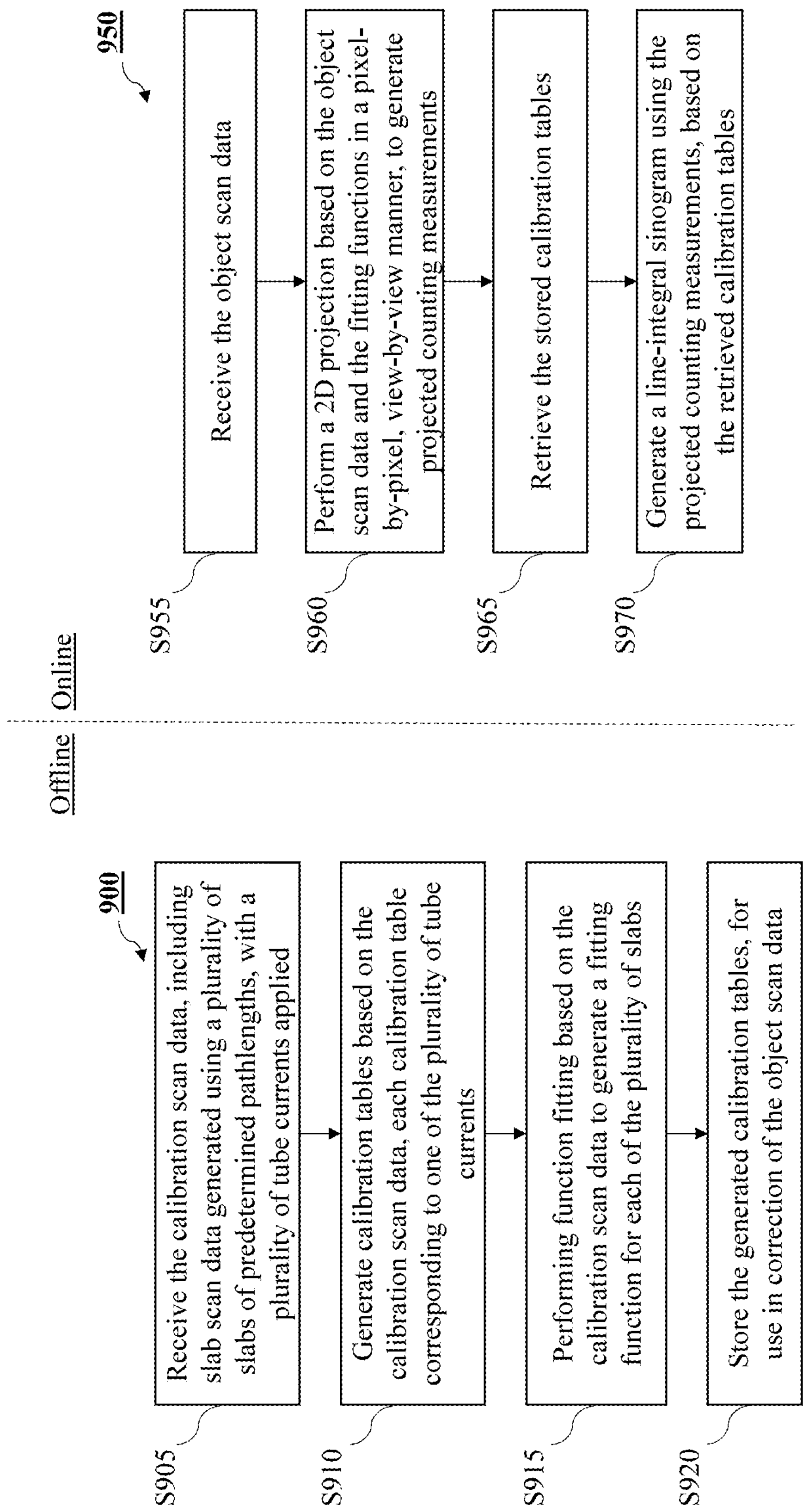
FIG. 9 shows a flow chart of an object scan data correction process including an offline portion 900 and an online portion 950, according to embodiments of the disclosure.

FIG. 9 shows a flow chart of an object scan data correction process, including an offline portion 900 and an online portion 950, according to embodiments of the disclosure. In step S905, the calibration scan data is received, including the slab scan data generated using a plurality of slabs of predetermined attenuation pathlengths, with a plurality of tube currents applied to the X-ray tube. In step S910, function fitting is performed based on the calibration scan data to generate a fitting function for each of the plurality of slabs. In step S915, calibration tables are generated based on the calibration scan data. Each calibration table corresponds to one of the plurality of tube currents. In step S920, the generated calibration tables are stored for use in the processing of the object scan data.

In step S955, the object scan data is received. In step S960, a two-dimensional projection is performed based on the object scan data and the fitting functions in a pixel-by-pixel, view-by-view manner, to generated projected counting measurements. In step S965, the stored calibration tables are retrieved. In step S970, a line-integral sinogram is generated using the projected counting measurements, based on the retrieved calibration tables.

In the approach described in the above embodiment, polynomial fitting functions determined based on the calibration scan data are used to project counting measurements acquired from the object scan to the nearest calibration tube current points. This ensures the accuracy of applying the calibration tables prepared for discrete, fixed tube current points in subsequent data processing and correction.

In an alternative embodiment of the disclosure, the polynomial fitting functions are used to prepare calibration tables at more refined tube current points, while the object scan data remains unchanged. In other words, based on the fitting functions, calibration data at certain unapplied tube current points within a potential tube current range of the object scan can be estimated, and additional calibration tables can be created for these tube current points. Subsequently, both the calibration tables generated using the calibration data and the additional calibration tables generated using the estimated calibration data can be applied in the data processing and correction of the object scan data. This approach eliminates the need for performing the two-dimensional projections on the object scan data, thereby reducing the data processing time at the online end.

Figure 10:
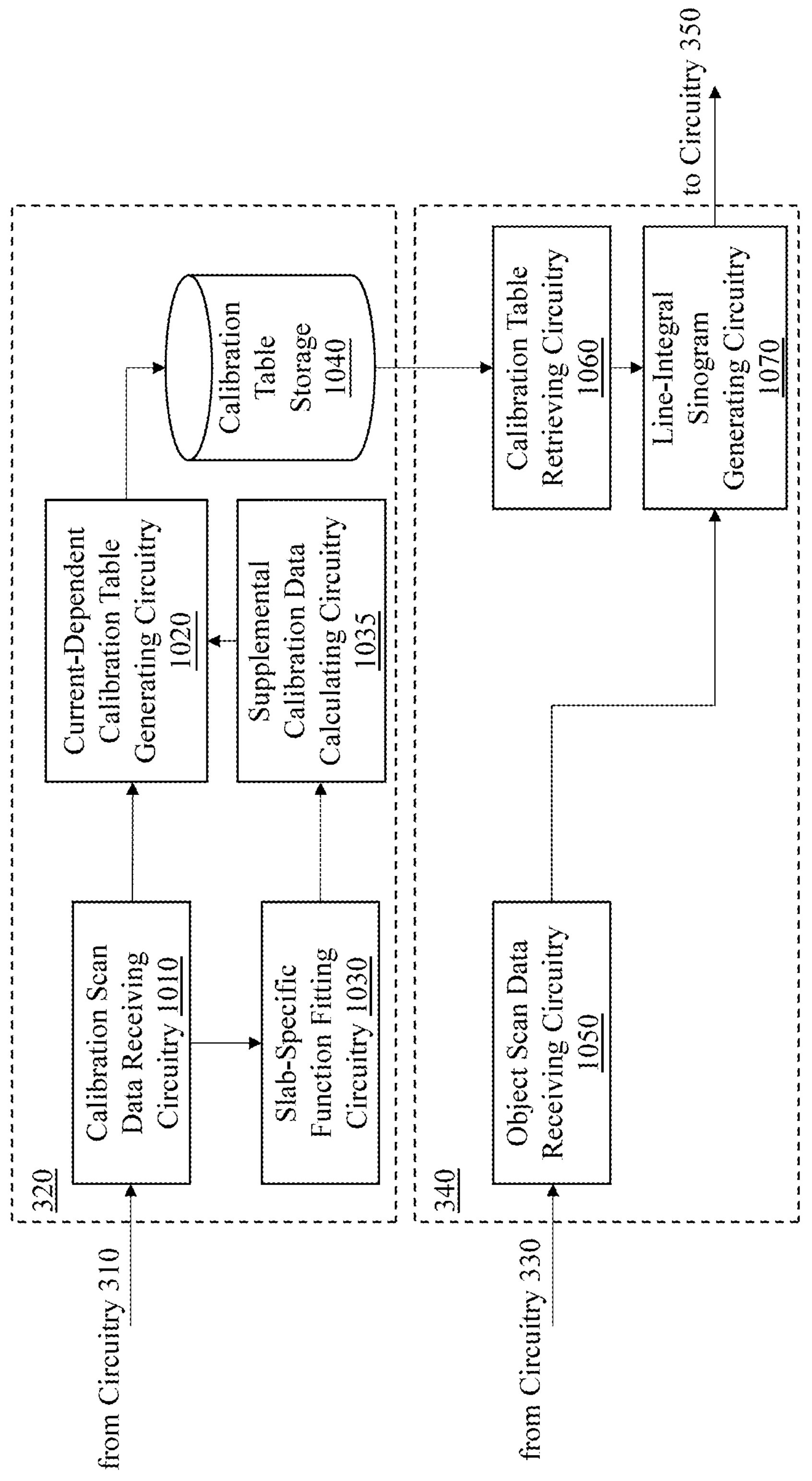
FIG. 10 shows a block diagram of calibration scan data processing circuitry 320 and object scan data correction circuitry 340 according to embodiments of the disclosure.

FIG. 10 shows a block diagram of calibration scan data processing circuitry 320 and object scan data correction circuitry 340 according to one embodiment of the disclosure. The calibration scan data processing circuitry 320 includes calibration scan data receiving circuitry 1010, current-dependent calibration table generating circuitry 1020, slab-specific function fitting circuitry 1030, supplemental calibration data calculating circuitry 1035, and calibration table storage 1040. The object scan data correction circuitry 340 includes object scan data receiving circuitry 1050, calibration table retrieving circuitry 1060, and line-integral sinogram generating circuitry 1070. The structures and functions of the calibration scan data receiving circuitry 1010, the slab-specific function fitting circuitry 1030, the object scan data receiving circuitry 1050, the calibration table retrieving circuitry 1060, and the line-integral sinogram generating circuitry 1070 can be identical to those of corresponding components shown in FIG. 5.

The supplemental calibration data calculating circuitry 1035 receives the generated fitting functions from the slab-specific function fitting circuitry 1030. Using these fitting functions, the supplemental calibration data calculating circuitry 1035 calculates supplemental calibration data for specific tube currents that are not applied during the slab scans, and sends the calculated data to the current-dependent calibration table generating circuitry 1020. The current-dependent calibration table generating circuitry 1020 not only generates calibration tables for tube current points used during the slab scans, but also uses the calculated supplemental calibration data to generate calibration tables for the unapplied tube currents.

Figure 11:
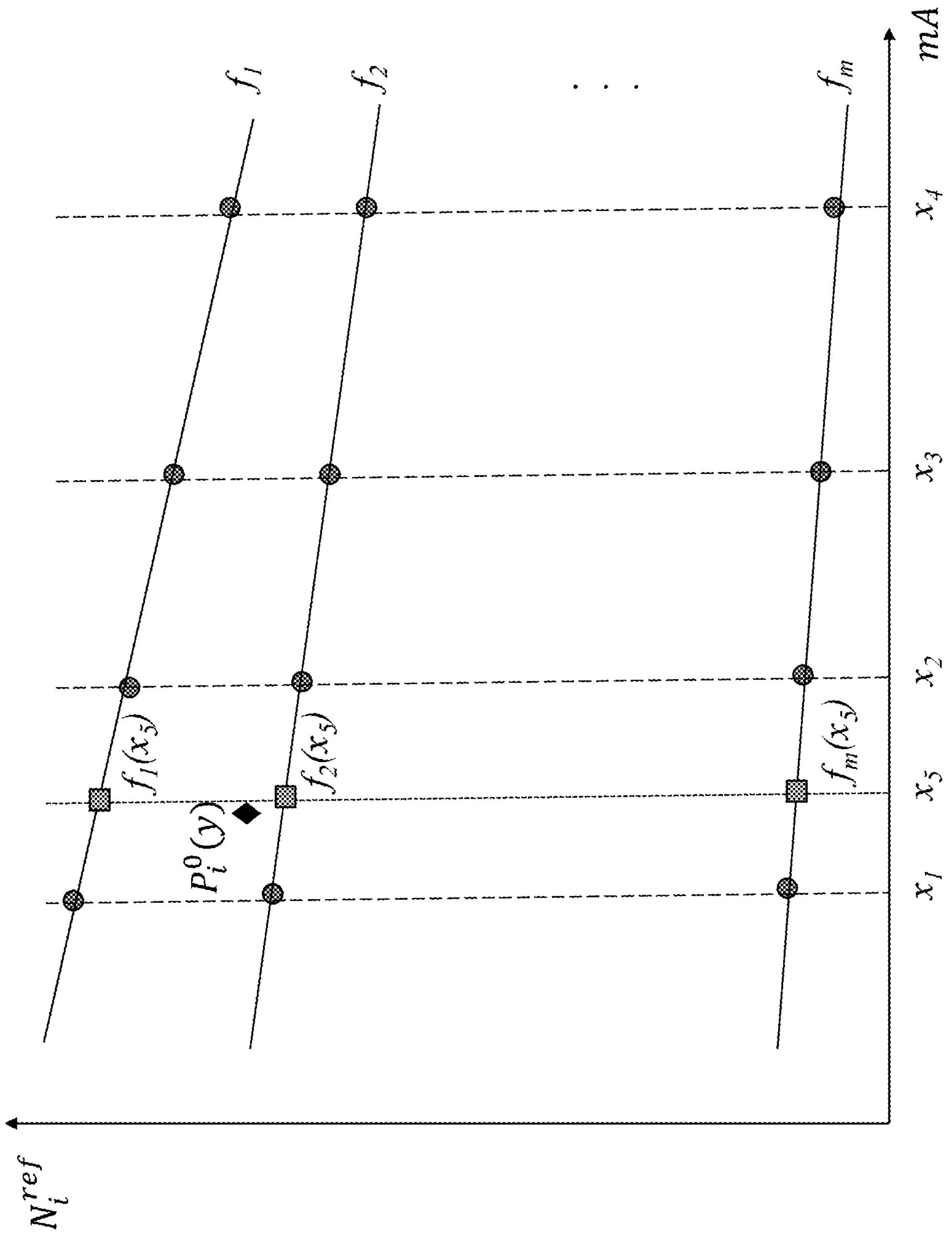
FIG. 11 shows exemplary calculation of supplemental calibration data using the fitting functions, according to embodiments of the disclosure.

FIG. 11 illustrates an example of calculating supplemental calibration data using the fitting functions according to embodiments of the disclosure. In FIG. 11, for a tube current point $x_5$ between the tube current points $x_1$ and $x_2$ applied during the slab scans, supplemental counting measurements $f_1(x_5)$, $f_2(x_5)$, . . . $f_m(x_5)$ (denoted by squares) can be calculated based on the fitting functions $f_1$-$f_m$ (corresponding to slabs 1-m) generated from the measured slab data (denoted by circular dots). Then, an additional calibration table for the tube current $x_5$ can be generated using the supplemental counting measurements.

The counting measurement $$P_i^0(y)$$

(denoted by the symbol "♦") acquired from the object scan can be processed use the calibration table for $x_5$, instead of the calibration table for $x_1$. Compared with the applied tube current $x_1$, the unapplied tube current $x_5$ is closer to the tube current y used during the acquisition of the corresponding view, thereby enhancing the calibration accuracy.

Furthermore, supplemental calibration data can be calculated at a plurality of unapplied tube current points distributed across the object scan's tube current range. This allows for preparing calibration tables for more tube current points, without extending the calibration time. By generating a sufficient fine calibration grid across the potential tube current range of the object scan, errors in data processing and correction of the object scan data can be suppressed.

Compared with the embodiments shown in FIGS. 5 and 9, the advantage of this embodiment is that more computation is completed prior to the object scans. This reduces the online scan data processing time, and makes it easier to meet the clinical workflow requirements.

There are also other methods to calculate supplemental calibration data for the unapplied tube current points, including piece-wise interpolation based on two adjacent tube current points, and more advanced fitting functions or interpolation schemes, such as cubic splines using more neighboring measurements. The fitting functions are not limited to polynomials; various functions that can accurately describe the data behavior along the tube current axis can also be used.

Similar to the embodiment shown in FIGS. 5 and 9, in this embodiment, the fitting functions and methods can differ for the counting imaging mode and the spectral imaging mode, as well as for individual energy bins in the spectral imaging mode.

Figure 12:
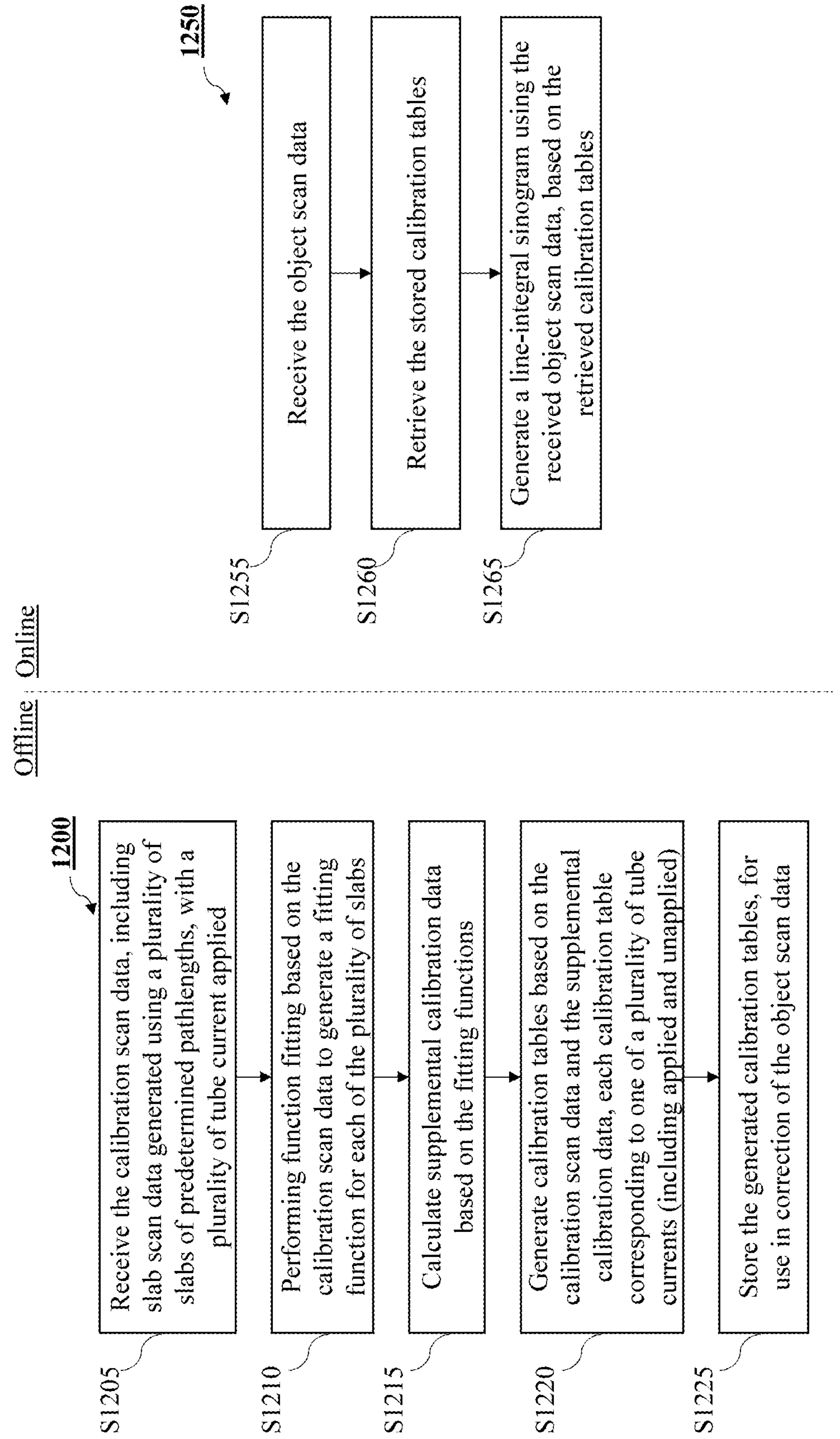
FIG. 12 shows a flow chart of an object scan data correction process including an offline portion 1200 and an online portion 1250, according to embodiments of the disclosure.

FIG. 12 shows a flow chart of an object scan data correction process, including an offline portion 1200 and an online portion 1250, according to embodiments of the disclosure. The offline portion 1200 starts at step S1205 by receiving the calibration scan data, including slab scan data generated using a plurality of slabs of predetermined pathlength, with a plurality of tube current applied to the X-ray tube. In step S1210, function fitting is performed based on the calibration scan data to generate a fitting function for each slab. In step S1215, supplemental calibration data is calculated for one or more unapplied tube currents, based on the fitting functions. In step S1220, calibration tables are generated based on the calibration scan data and the supplemental calibration data. Each calibration table corresponds to one tube current, including both the applied and unapplied ones. In step S1225, the generated calibration tables are stored for use in correction of the object scan data.

The online portion 1250 starts at step S1255 by receiving the object scan data. In step S1260, the stored calibration tables are retrieved. In step S1265, a line-integral sinogram is generated using the received object scan data, based on the retrieved calibration tables. By using calibration tables corresponding to the closest tube current points, selected from both the original and supplemental calibration tables, the correction accuracy of the object scan data can be significantly improved.

Other methods can be used to create additional calibration tables for unapplied tube current points. For example, these calibration tables can be generated by interpolating the existing calibration tables prepared for adjacent tube current points that are applied during the calibration scan.

Figure 13:
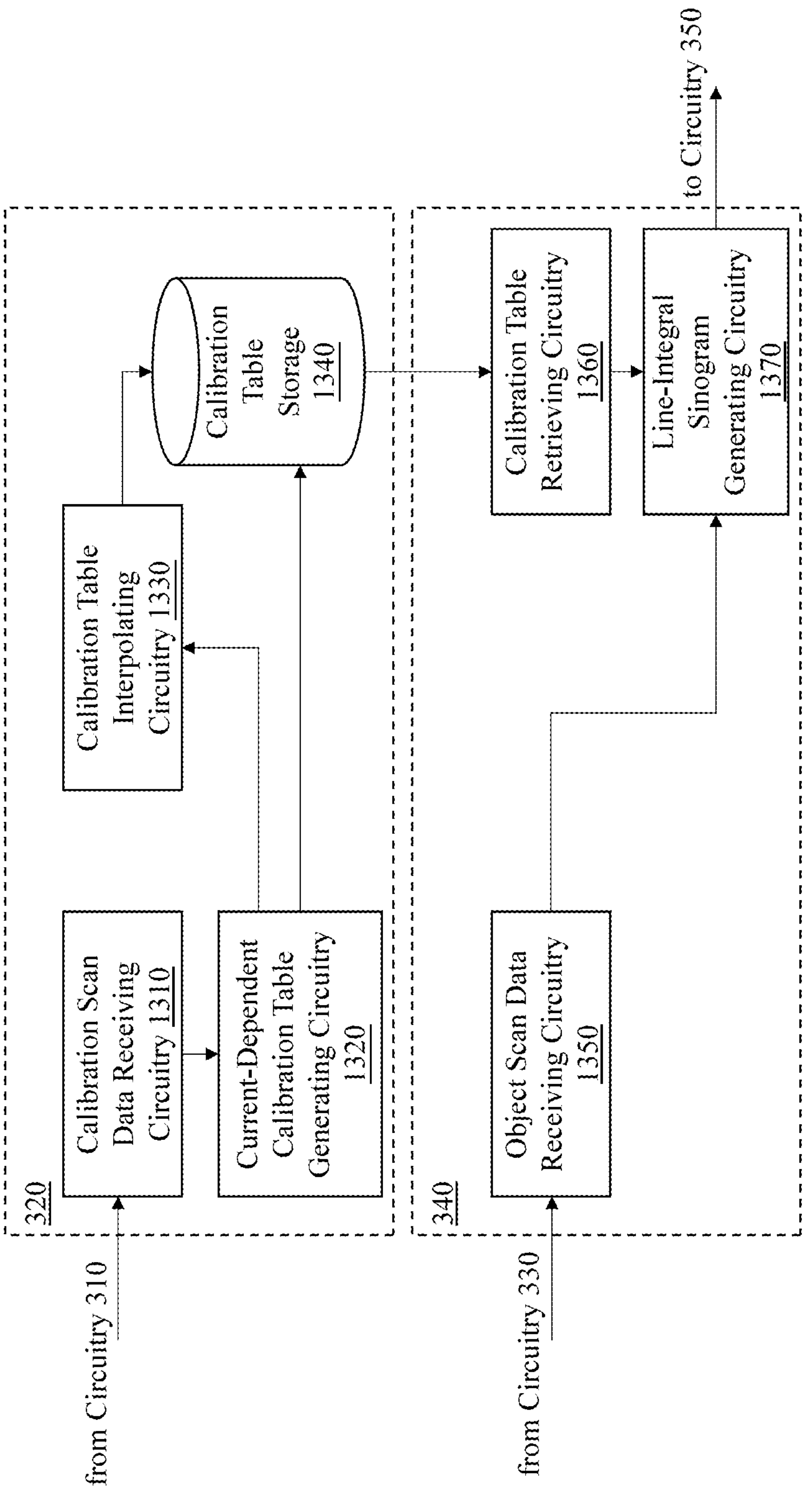
FIG. 13 shows a block diagram of calibration scan data processing circuitry 320 and object scan data correction circuitry 340 according to embodiments of the disclosure.

FIG. 13 shows a block diagram of calibration scan data processing circuitry 320 and object scan data correction circuitry 340 according to one embodiment of the disclosure. The calibration scan data processing circuitry 320 includes calibration scan data receiving circuitry 1310, current-dependent calibration table generating circuitry 1320, calibration table interpolating circuitry 1330, and calibration table storage 1340. The object scan data correction 340 includes object scan data receiving circuitry 1350, calibration table retrieving circuitry 1360, and line-integral sinogram generating circuitry 1370. The structures and functions of the calibration scan data receiving circuitry 1310, the current-dependent calibration table generating circuitry 1320, the object scan data receiving circuitry 1350, the calibration table retrieving circuitry 1360, and the line-integral sinogram generating circuitry 1370 can be identical to those of corresponding components shown in FIG. 5.

The calibration table interpolating circuitry 1330 obtains the calibration tables generated for the applied tube current points from the current-dependent calibration table generating circuitry 1320, and performs interpolation on the obtained calibration tables to generate supplemental calibration tables for the unapplied tube current points. The calibration tables generated by both the current-dependent calibration table generating circuitry 1320 and the calibration table interpolating circuitry 1330 are stored in the calibration table storage 1340, for use in processing and correction of the object scan data.

For instance, assuming the PCD forward model at a calibration tube current point mA1 is $$N_1 = FW_1(S_0, D) \tag{12}$$

and the forward model at an adjacent calibration tube current point mA2 is $$N_1 = FW_2(S_0, D) \tag{13}$$

Therefore, for a tube current x between mA1 and mA2, the forward model can be expressed as a linear combination of $FW_1$ and $FW_2$, where $S_0$ and D are the tunable components of the forward model with calibrated parameters from the slab data:

$$N_i^{AEC} = cFW_1 + (1-c)FW_2 \tag{14}$$

The coefficient c can be determined based on the value of the tube current x, as follows:

$$c = (mA2 - x)/(mA2 - mA1) \tag{15}$$

Interpolation of the AEC forward model is not limited to the linear method in Equation (14); any forms based on neighboring tube current points can be used. By completing more computation prior to the object scans, the online scan data processing time can be reduced compared with the embodiment shown in FIGS. 5 and 9.

Figure 14:
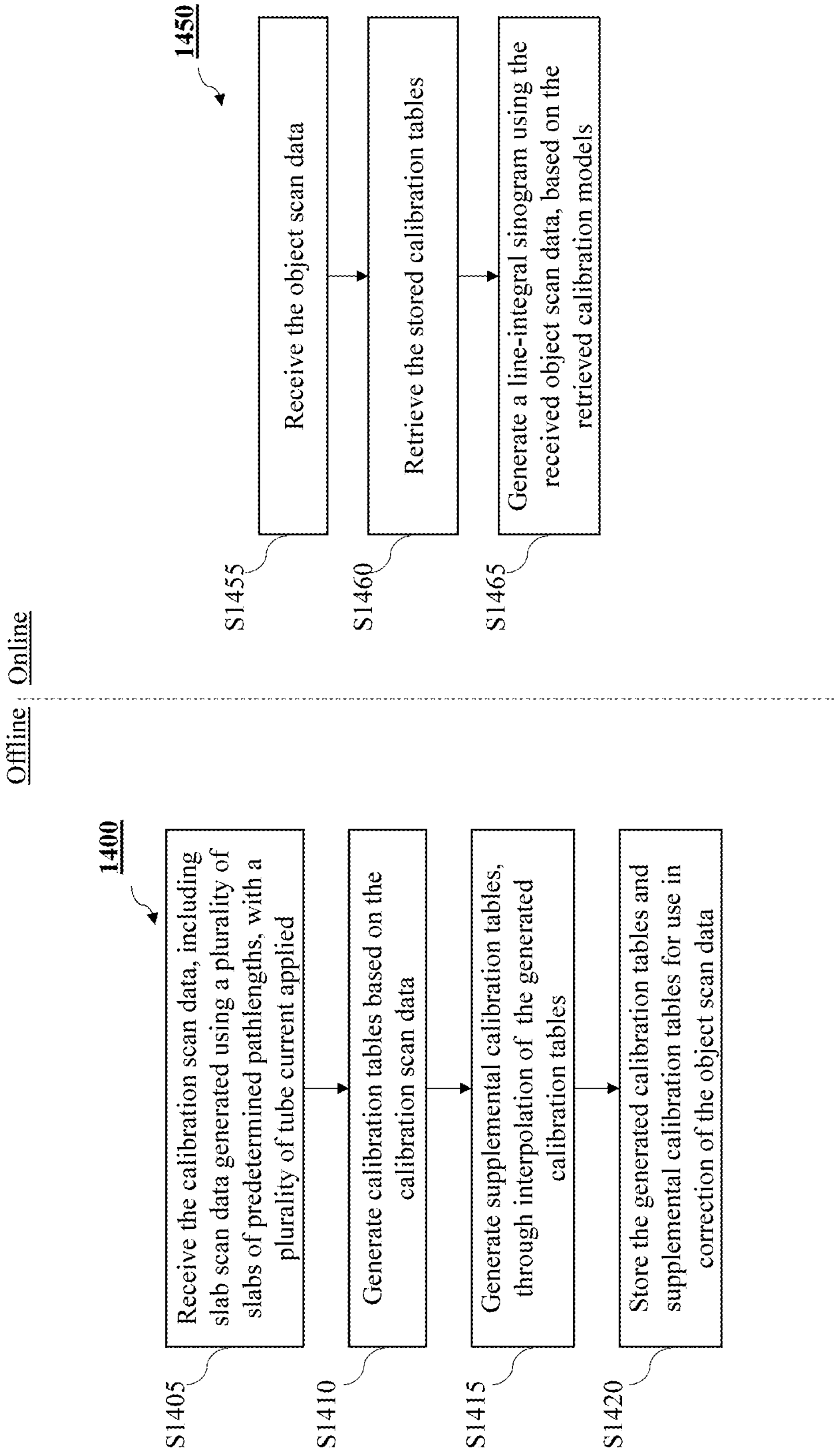
FIG. 14 shows a flow chart of an object scan data correction process including an offline portion 1400 and an online portion 1450, according to embodiments of the disclosure.

FIG. 14 shows a flow chart of an object scan data correction process, including an offline portion 1400 and an online portion 1450, according to one embodiment of the disclosure. The offline portion 1400 starts at step S1405 by receiving the calibration scan data, including slab scan data generated using a plurality of slabs of predetermined pathlength with a plurality of tube current applied to the X-ray tube. In step S1410, calibration tables are generated based on the calibration scan data. In step S1415, supplemental calibration tables are generated through interpolation of the generated calibration tables. In step S1420, the generated calibration tables and the supplemental calibration tables are stored for use in correction of the object scan data.

The online portion 1450 starts at step S1455 by receiving the object scan data. In step S1460, the stored calibration tables are retrieved. In step S1465, a line-integral sinogram is generated using the received object scan data, based on the retrieved calibration tables.

There is no limitation on the methods used to generate the AEC tube current profiles for the object scan. Instead, various methods are available, such as using a scout scan to estimate the imaging object's 3D pathlength profile, and then generating the tube current profiles for the scan regions accordingly.

The embodiments described in the disclosure can be used in a photon-counting CT scanner system, said CT scanner system comprising one or more X-ray tubes that emit X-ray radiation, and an array of detector pixels for receiving the X-ray radiation propagating through a field of view (FOV) of the CT scanning system. The detector response correction scheme can be applied to both the PCD counting and the spectral forward models.

Figure 15:
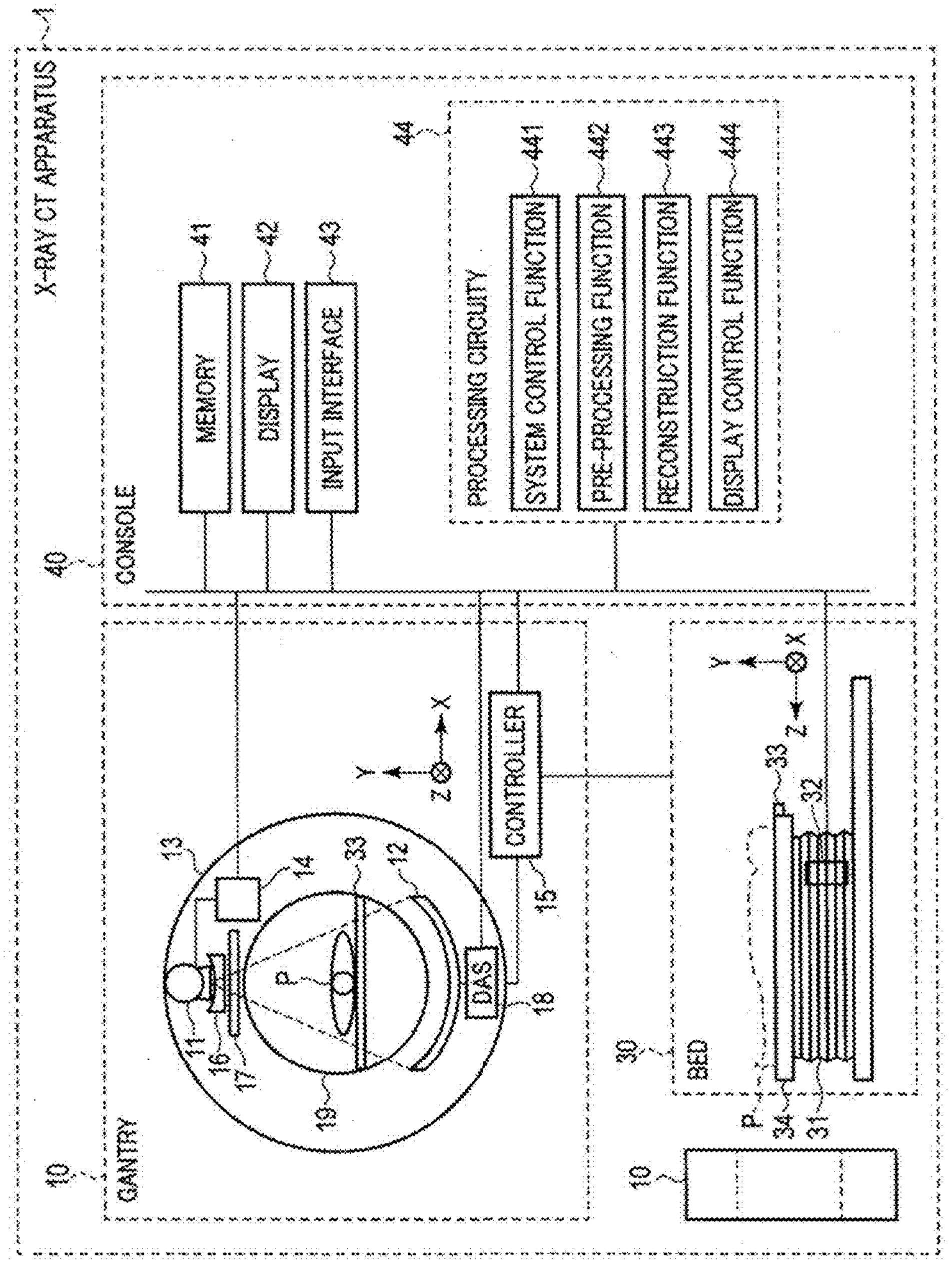
FIG. 15 shows an example of a photon-counting Computed Tomography scanner system that can incorporate the techniques disclosed herein.

The detector response correcting approach can be implemented in a photon-counting CT scanning system as described below with reference to FIG. 15. The X-ray CT apparatus 1 shown in FIG. 15 includes a gantry 10, a bed 30, and a console 40 that implements the processing of the medical imaging processing apparatus. For the sake of explanation, FIG. 13 shows multiple gantries 10.

In the present embodiment, the rotation axis of a rotation frame 13 in the non-tilted state, or the longitudinal direction of a tabletop 33 of the bed 30, is defined as a "Z-axis direction;" the axial direction orthogonal to the Z-axis direction and horizontal to the floor is defined as an "X-axis direction;" and the axial direction orthogonal to the Z-axis direction and vertical to the floor is defined as a "Y-axis direction."

For example, the gantry 10 and the bed 30 are installed in a CT examination room, and the console 40 is installed in a control room adjacent to the CT examination room. The console 40 is not necessarily installed in the control room. For example, the console 40 can be installed together with the gantry 10 and the bed 30 in the same room. In any case, the gantry 10, the bed 30, and the console 40 are communicably connected to one another by wire or radio.

The gantry 10 is a scanner with a configuration for performing X-ray CT imaging on a subject (or an imaging object) P. The gantry 10 includes an X-ray tube 11, an X-ray detector 12, a rotation frame 13, an X-ray high voltage device 14, a controller 15, a wedge filter 16, a collimator 17, and a data acquisition system (DAS) 18.

The X-ray tube 11 is a vacuum tube that generates X-rays by emitting thermal electrons from the cathode (filament) to the anode (target) in response to application of a high voltage and supply of a filament current from the X-ray high voltage device 14. Specifically, X-rays are generated by the thermal electrons colliding with the target. Examples of the X-ray tube 11 include a rotating anode type X-ray tube that generates X-rays by emitting thermal electrons to the rotating anode. The X-rays generated in the X-ray tube 11 are, for example, formed into a cone-beam shape by the collimator 17, and applied to the subject P.

The X-ray detector 12 detects X-rays that have been emitted by the X-ray tube 11 and have passed through the subject P, and outputs an electrical signal corresponding to the X-ray dose to the DAS 18. The X-ray detector 12 includes a plurality of X-ray detection element lines, each including a plurality of X-ray detection elements aligned in the channel direction (the X-axis direction, or the column direction) along an are having a center at the focus of the X-ray tube 11, for example. The X-ray detector 12 has an array structure in which a plurality of X-ray detection element lines, each including a plurality of X-ray detection elements aligned in the channel direction, are aligned in the segment direction (the Z-axis direction, or the row direction).

Specifically, the X-ray detector 12 can be, for example, a direct conversion type detector including a semiconductor element that converts incident X-rays into an electrical signal. The X-ray detector 12 is an example of the PCD according to the present embodiment, and will also be referred to as a "PCD 12."

The rotation frame 13 supports an X-ray generator and the X-ray detector 12 rotatably around a rotation axis. Specifically, the rotation frame 13 is an annular frame that supports the X-ray tube 11 and the X-ray detector 12 in such a manner that the X-ray tube 11 faces the X-ray detector 12, and rotates the X-ray tube 11 and the X-ray detector 12 under the control of a controller 15 to be described later. The rotation frame 13 is rotatably supported by a stationary frame (not shown) made of a metal such as aluminum. Specifically, the rotation frame 13 is connected to an edge portion of the stationary frame via a bearing. The rotation frame 13 rotates around the rotation axis Z at a predetermined angular velocity while receiving power from a driver of the controller 15.

In addition to the X-ray tube 11 and the X-ray detector 12, the rotation frame 13 includes and supports the X-ray high voltage device 14 and the DAS 18. Such a rotation frame 13 is housed in an approximately-cylindrical case with a bore 19 constituting an imaging space. The bore approximately corresponds to the FOV. The central axis of the bore corresponds to the rotation axis Z of the rotation frame 13. Detection data generated by the DAS 18 is transmitted, for example, from a transmitter (not shown) to a receiver (not shown) arranged on a non-rotating portion (such as the stationary frame, illustration omitted in FIG. 13) of the gantry, and then transferred to the console 40.

The X-ray high voltage device 14 includes: a high voltage generator including electrical circuitry such as a transformer, a rectifier, etc. and having the function of generating a high voltage to be applied to the X-ray tube 11 and a filament current to be supplied to the X-ray tube 11; and an X-ray controller configured to control an output voltage in accordance with the X-rays emitted by the X-ray tube 11. The high voltage generator can be of a transformer type, or an inverter type. The X-ray high voltage device 14 may be provided in the rotation frame 13 to be described later, or in the stationary frame (not shown) of the gantry 10.

The controller 15 includes processing circuitry including a central processing unit (CPU), etc., and a driver such as a motor or an actuator, etc. The processing circuitry includes, as hardware resources, a processor, such as a CPU or a micro processing unit (MPU), and a memory, such as a read only memory (ROM) or a random access memory (RAM). The controller 15 can be realized by an application specific integrated circuit (ASIC), a field programmable gate array (FPGA), or another complex programmable logic device (CPLD) or simple programmable logic device (SPLD). The controller 15 controls the X-ray high voltage device 14 and the DAS 18, etc. in accordance with instructions from the console 40. The processor implements the above control by reading and executing a program stored in the memory.

The CPU can execute a computer program including a set of computer-readable instructions that perform the functions described herein, and the program is stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor and an operating system known to those skilled in the art. Further, the CPU can be implemented as multiple processors cooperatively working in parallel to perform the instructions.

The controller 15 also has the function of performing operation control of the gantry 10 and the bed 30 in response to an input signal from an input interface 43 to be described later attached to the console 40 or the gantry 10. For example, the controller 15 performs control to rotate the rotation frame 13, control to tilt the gantry 10, or control to operate the bed 30 and the tabletop 33 in response to an input signal. The control to tilt the gantry 10 is implemented by the controller 15 rotating the rotation frame 13 around an axis parallel to the X-axis direction, based on tilt angle information input through the input interface 43 attached to the gantry 10. The controller 15 may be provided either in the gantry 10 or in the console 40. The controller 15 may be configured by directly integrating a program in the circuitry of the processor, instead of storing a program in the memory. In this case, the processor implements the above-described control by reading and executing the program integrated in the circuitry.

The wedge filter 16 is a filter for adjusting the dose of X-rays emitted from the X-ray tube 11. Specifically, the wedge filter 16 is a filter that allows X-rays emitted from the X-ray tube 11 to pass therethrough, and attenuates the X-rays so that the X-rays emitted from the X-ray tube 11 to the subject P exhibit predetermined distribution. For example, the wedge filter 16 (or bow-tie filter) is a filter obtained by processing aluminum so that it has a predetermined target angle and a predetermined thickness.

The collimator 17 is lead plates or the like for narrowing the application range of X-rays that have passed through the wedge filter 16, and includes a slit formed by combining the lead plates or the like. The collimator 17 may be referred to as an "X-ray diaphragm."

The DAS 18 generates digital data indicating counts of X-rays detected by the X-ray detector 12 (also referred to as "detection data") for each of a plurality of energy bands (referred to as "energy bins" or simply as "bins"). The detection data is a set of a channel number and row number of a source X-ray detection element, a view number indicating a collected view (also referred to as a projection angle), and data of the count value identified by the energy bin number. The DAS 18 is implemented by, for example, an application specific integrated circuit (ASIC) on which a circuit element capable of generating detection data is mounted. The detection data is transferred to the console 40.

The bed 30 is a device to place thereon the subject P to be scanned and move the subject P, and includes a base 31, a bed actuator 32, a tabletop 33, and a support frame 34.

The base 31 is a case that supports the support frame 34 movably in the vertical direction.

The bed actuator 32 is a motor or actuator that moves the tabletop 33 on which the subject P is placed in the longitudinal direction of the tabletop 33. The bed actuator 32 moves the tabletop 33 in accordance with control by the console 40 or control by the controller 15. For example, the bed actuator 32 moves the table top 33 in the direction orthogonal to the subject P so that the body axis of the subject P placed on the table top 33 matches the central axis of the bore of the rotation frame 13. The bed actuator 32 may also move the tabletop 33 in the body axis direction of the subject P in accordance with X-ray CT imaging performed using the gantry 10. The bed actuator 32 generates power by driving at a rotation speed corresponding to the duty ratio of the drive signal from the controller 15. The bed actuator 32 is implemented by a motor, such as a direct drive motor or a servo motor.

The tabletop 33 provided on the top surface of the support frame 34 is a plate on which the subject P is placed. The bed actuator 32 may move not only the tabletop 33 but the support frame 34 in the longitudinal direction of the tabletop 33.

The console 40 includes a memory 41, a display 42, an input interface 43, and processing circuitry 44. Data communication between the memory 41, the display 42, the input interface 43, and the processing circuitry 44 is performed via a bus. The console 40 is described as being separate from the gantry 10, but the gantry 10 may include the console 40 or part of each constituent element of the console 40.

The memory 41 is a storage device, such as a hard disk drive (HDD), a solid state drive (SSD), or an integrated circuit storage device, etc., which stores various types of information. The memory 41 stores, for example, projection data and reconstructed image data. The memory 41 may be not only the HDD, SSD, or the like, but a driver that writes and reads various types of information in and from, for example, a portable storage medium such as CD, DVD, or a flash memory, or a semiconductor memory such as a random access memory (RAM). The storage area of the memory 41 may be in the X-ray CT apparatus 1, or in an external storage device connected via the network. For example, the memory 41 stores data of a CT image or a display image. The memory 41 also stores a control program according to the present embodiment.

The display 42 displays various types of information. For example, the display 42 outputs a graphical user interface (GUI) or the like for receiving a medical image (CT image) generated by the processing circuitry 44, and various types of operations from the operator. For the display 42, for example, a liquid crystal display (LCD), a cathode ray tube (CRT) display, an organic electro luminescence display (OELD), a plasma display, or any other display can be used as appropriate. The display 42 may be provided in the gantry 10. The display 42 may either be a desktop type or configured by a tablet device capable of wirelessly communicating with the console 40.

The input interface 43 receives various types of input operations from the operator, converts a received input operation into an electrical signal, and outputs the electrical signal to the processing circuitry 44. For example, the input interface 43 receives, from the operator, a collection condition for collecting projection data, a reconstruction condition for reconstructing a CT image, and an image-processing condition for generating a post-processing image from the CT image, etc. For the input interface 43, for example, a mouse, a keyboard, a trackball, a switch, a button, a joystick, a touch pad, or a touch panel display can be used as appropriate. In the present embodiment, the input interface 43 does not necessarily include a physical operation component such as a mouse, a keyboard, a trackball, a switch, a button, a joystick, a touch pad, or a touch panel display. For example, the input interface 43 also includes electrical signal processing circuitry that receives an electrical signal corresponding to an input operation from an external input device provided separately from the apparatus, and outputs the electrical signal to the processing circuitry 44. The input interface 43 may be provided in the gantry 10. The input interface 43 may be configured by a tablet device capable of wirelessly communicating with the console 40.

The processing circuitry 44 controls the overall operation of the X-ray CT apparatus 1 in accordance with the electrical signal of the input operation output from the input interface 43. For example, the processing circuitry 44 includes, as hardware resources, a processor such as a CPU, an MPU, or a graphics processing unit (GPU), and a memory such as a ROM or a RAM. With a processor that executes a program loaded into the memory, the processing circuitry 44 performs a system control function 441, a pre-processing function 442, a reconstruction function 443, and a display control function 444. Each of the functions (the system control function 441, the pre-processing function 442, the reconstruction function 443, and the display control function 444) is not necessarily implemented by a single processing circuit. Processing circuitry can be configured by combining a plurality of independent processors, and the processors can execute respective programs to implement the functions.

The system control function 441 controls each function of the processing circuitry 44 based on an input operation received from the operator via the input interface 43. Specifically, the system control function 441 reads a control program stored in the memory 41, loads it into a memory in the processing circuitry 44, and controls each part of the X-ray CT apparatus 1 in accordance with the loaded control program. For example, the processing circuitry 44 performs each function of the processing circuitry 44 based on an input operation received from the operator via the input interface 43. For example, the system control function 441 obtains a two-dimensional positioning image of the subject P to determine the scan range, imaging condition, etc. The positioning image can also be referred to as a "scanogram" or "scout image."

The pre-processing function 442 generates data obtained by performing pre-processing on detection data output from the DAS 18. Data (detection data) before pre-processing and data after pre-processing can be collectively referred to as "projection data." The pre-processing function 442 is an example of the pre-processor.

The reconstruction function 443 generates CT image data by performing reconstruction processing using a filtered back projection method, a successive approximation reconstruction method, a stochastic image reconstruction method, or the like, on the projection data generated by the pre-processing function 442. The reconstruction function 443 is an example of the reconstruction processor. Image filtering, smoothing, volume rendering, or image differential processing can be applied to the CT image data if required. The display control function 444 converts CT image data generated by the reconstruction function 443 into tomographic image data of a given cross section, or three-dimensional image data by a publicly-known method, based on the input operation received from the operator via the input interface 43. The generation of three-dimensional image data can be performed directly by the reconstruction function 443. The display control function 444 is an example of the display controller.

In one implementation, the X-ray tube 11 is a single source emitting a broad spectrum of X-ray energies, and the PCD 12 can use a direct X-ray radiation detectors based on semiconductors, such as cadmium telluride (CdTe), cadmium zinc telluride (CZT), silicon (Si), mercuric iodide ($HgI2$), and gallium arsenide (GaAs). As mentioned above, semiconductor-based direct X-ray detectors generally have much faster time response than indirect detectors, such as scintillator detectors. The fast time response of direct detectors enables them to resolve individual X-ray detection events, although at the high X-ray fluxes typical in clinical X-ray applications, some pileup of detection events may occur. The energy of a detected X-ray is proportional to the signal generated by the direct detector, and the detection events can be organized into energy bins yielding spectrally resolved X-ray data for spectral CT.

Numerous modifications and variations of the embodiments presented herein are possible in light of the above teachings. It is therefore to be understood that within the scope of the claims, the application may be practiced otherwise than as specifically described herein. The inventions are not limited to the examples that have just been described; it is in particular possible to combine features of the illustrated examples with one another in variants that have not been illustrated.

Embodiments of the present disclosure may also be as set forth in the following parentheticals.

(1) A method for performing object scan data correction in an X-ray imaging system having a photon-counting detector, the X-ray imaging system including an X-ray tube for emitting X-rays, the method comprising: acquiring calibration scan data from a calibration scan performed using a plurality of slabs; performing function fitting based on the acquired calibration scan data to generate a plurality of fitting functions corresponding to the plurality of slabs, each corresponding fitting function representing a relationship between a counting measurement detected with respect to one slab of the plurality of slabs and a tube current applied to the X-ray tube; establishing a calibration table based on the acquired calibration scan data; acquiring object scan data from an object scan performed on an imaging object; performing data correction for the acquired object scan data, based on the established calibration table and the generated plurality of fitting functions; and reconstructing an image of the imaging object based on the performed data correction.

(2) The method of (1), wherein the step of acquiring the calibration scan data further comprises acquiring the calibration scan data from the calibration scan performed using each slab of the plurality of slabs, with a first number ($n_1$) of tube currents applied to the X-ray tube, the establishing step further comprises: establishing, based on the acquired calibration scan data, the first number ($n_1$) of sub-calibration tables to form the established calibration table, each sub-calibration table corresponding to one tube current of the first number ($n_1$) of tube currents, and storing the first number ($n_1$) of sub-calibrations tables, for use in performing the data correction, the step of performing the data correction further comprises: for each view of the acquired object scan data, projecting a counting measurement detected by each pixel of the photon-counting detector, based on the generated plurality of fitting functions, to a projected counting measurement, as if the projected counting measurement were detected when a specific tube current of the first number ($n_1$) of tube currents is applied to the X-ray tube, and using the projected counting measurements to generate a line-integral sinogram, based on the first number ($n_1$) of sub-calibration tables, and the reconstructing step further comprises reconstructing the image of the imaging object, based on the generated line-integral sinogram.

(3) The method of (2), wherein the X-ray imaging system further comprises a tube current detector configured to directly or indirectly detect a tube current applied to the X-ray tube during the object scan, and the projecting step further comprises: for each view of the acquired object scan data, based on a counting measurement detected by each pixel of the photon-counting detector and a corresponding tube current detected when the view is acquired, using at least one fitting function of the generated plurality of fitted functions, to derive a corresponding fitting function with respect to an attenuation pathlength corresponding to the counting measurement, and calculating, based on the derived corresponding fitting function, a counting measurement corresponding to one tube current of the first number ($n_1$) of tube currents that is closest to the corresponding tube current detected when the view is acquired, as the projected counting measurement.

(4) The method of (2), wherein the step of performing function fitting further comprises performing the function fitting based on the acquired calibration scan data to generate a corresponding polynomial fitting function with respect to each slab of the plurality of slabs, and a number of order of the corresponding polynomial fitting function is determined based on the first number ($n_1$).

(5) The method of (2), wherein the step of generating the line-integral sinogram further comprises, generating a counting line-integral sinogram when the X-ray imaging system operates in a counting imaging mode, and generating a basis material line-integral sinogram when the X-ray imaging system operates in a material decomposition imaging mode, and the step of performing function fitting further comprises, when the X-ray imaging system operates in the material decomposition imaging mode, for each slab of the plurality of slabs, generating respective fitting functions specific to individual energy bins.

(6) The method of (1), wherein the step of acquiring the calibration scan data further comprises acquiring the calibration scan data from the calibration scan performed using each slab of the plurality of slabs, where the plurality of slabs have different attenuation pathlengths from one another, and an attenuation pathlength step among the plurality of slabs is not larger than a predetermined threshold.

(7) The method of (1), wherein the step of establishing the calibration table further comprises establishing, based on the acquired calibration scan data, a particular calibration table for calibrating a detector response of the X-ray imaging system and/or for correcting a pile-up effect of the X-ray imaging system.

(8) The method of (1), wherein the step of acquiring the calibration scan data further comprises acquiring the calibration scan data from the calibration scan performed using each slab of the plurality of slabs, with a first number ($n_1$) of tube currents applied to the X-ray tube, the establishing step further comprises, calculating supplemental calibration data based on the generated plurality of fitting functions, as if the supplemental calibration data were acquired from a calibration scan performed on each slab of the plurality of slabs, with a second number ($n_2$) of tube currents applied to the X-ray tube, where the second number ($n_2$) of tube currents are different from the first number ($n_1$) of tube currents, establishing, based on the acquired calibration scan data and the calculated supplemental calibration data, a third number ($n_3$) of sub-calibration tables to form the established calibration table, each sub-calibration table corresponding to one tube current of the first number ($n_1$) and second number ($n_2$) of tube currents, where $n_3=n_1+n_2$, and storing the third number ($n_3$) of sub-calibrations tables, for use in the data correction, the step of performing the data correction for the acquired object scan data further comprising using the acquired object scan data to generate a line-integral sinogram, based on the third number ($n_3$) of sub-calibrations tables, and the reconstructing step further comprises reconstructing the image of the imaging object, based on the generated line-integral sinogram.

(9) The method of (8), wherein the step of calculating the supplemental calibration data further comprises, for each fitting function of the generated plurality of fitting functions, using the fitting function to calculate a counting measurement corresponding to each tube current of the second number ($n_2$) of tube currents, the first number ($n_1$) and second number ($n_2$) of tube currents are distributed across a tube current range applied during the object scan, and a tube current step among the first number ($n_1$) and second number ($n_2$) of tube currents is not larger than a predetermined threshold.

(10) An apparatus for performing object scan data correction in an X-ray imaging system having a photon-counting detector, the X-ray imaging system including an X-ray tube for emitting X-rays, the apparatus comprising: processing circuitry configured to acquire calibration scan data from a calibration scan performed using a plurality of slabs, perform function fitting based on the acquired calibration scan data to generate a plurality of fitting functions corresponding to the plurality of slabs, each corresponding fitting function representing a relationship between a counting measurement detected with respect to one slab of the plurality of slabs and a tube current applied to the X-ray tube, establish a calibration table based on the acquired calibration scan data, acquire object scan data from an object scan performed on an imaging object, perform data correction for the acquired object scan data, based on the established calibration table and the generated plurality of fitting functions, and reconstruct an image of the imaging object based on the performed data correction.

(11) The apparatus of (10), wherein the processing circuitry is further configured to: acquire the calibration scan data from the calibration scan performed using each slab of the plurality of slabs, with a first number ($n_1$) of tube currents applied to the X-ray tube, establish the calibration table by, establishing, based on the acquired calibration scan data, the first number ($n_1$) of sub-calibration tables to form the established calibration table, each sub-calibration table corresponding to one tube current of the first number ($n_1$) of tube currents, and storing the first number ($n_1$) of sub-calibrations tables, for use in performing the data correction, perform the data correction by: for each view of the acquired object scan data, projecting a counting measurement detected by each pixel of the photon-counting detector, based on the generated plurality of fitting functions, to a projected counting measurement, as if the projected counting measurement were detected when a specific tube current of the first number ($n_1$) of tube currents is applied to the X-ray tube, and using the projected counting measurements to generate a line-integral sinogram, based on the first number ($n_1$) of sub-calibration tables, and reconstruct the image of the imaging object, based on the generated line-integral sinogram.

(12) The apparatus of (11), wherein the X-ray imaging system further comprises a tube current detector configured to directly or indirectly detect a tube current applied to the X-ray tube during the object scan, and the processing circuitry is further configured to: for each view of the acquired object scan data, based on a counting measurement detected by each pixel of the photon-counting detector and a corresponding tube current detected when the view is acquired, use at least one fitting function of the generated plurality of fitted functions, to derive a corresponding fitting function with respect to an attenuation pathlength corresponding to the counting measurement, and calculate, based on the derived corresponding fitting function, a counting measurement corresponding to one tube current of the first number ($n_1$) of tube currents that is closest to the corresponding tube current detected when the view is acquired, as the projected counting measurement.

(13) The apparatus of (11), wherein the processing circuitry is further configured to perform the function fitting based on the acquired calibration scan data to generate a corresponding polynomial fitting function for each slab of the plurality of slabs, and a number of order of the corresponding polynomial fitting function is determined based on the first number ($n_1$).

(14) The apparatus of (11), wherein the processing circuitry is further configured to: generate a counting line-integral sinogram when the X-ray imaging system operates in a counting imaging mode, and generate a basis material line-integral sinogram when the X-ray imaging system operates in a material decomposition imaging mode, and when the X-ray imaging system operates in the material decomposition imaging mode, for each slab of the plurality of slabs, generate respective fitting functions specific to individual energy bins.

(15) The apparatus of (10), wherein the processing circuitry is further configured to acquire the calibration scan data from the calibration scan performed using each slab of the plurality of slabs, where the plurality of slabs have different attenuation pathlengths from one another, and an attenuation pathlength step among the plurality of slabs is not larger than a predetermined threshold.

(16) The apparatus of (10), wherein the processing circuitry is further configured to establish, based on the acquired calibration scan data, a particular calibration table for calibrating a detector response of the X-ray imaging system and/or for correcting a pile-up effect of the X-ray imaging system.

(17) The apparatus of (10), wherein the processing circuitry is further configured to: acquire the calibration scan data from the calibration scan performed using each slab of the plurality of slabs, with a first number ($n_1$) of tube currents applied to the X-ray tube, establish the calibration table by calculating supplemental calibration data based on the generated plurality of fitting functions, as if the supplemental calibration data were acquired from a calibration scan performed on each slab of the plurality of slabs, with a second number ($n_2$) of tube currents applied to the X-ray tube, where the second number ($n_2$) of tube currents are different from the first number ($n_1$) of tube currents, establishing, based on the acquired calibration scan data and the calculated supplemental calibration data, a third number ($n_3$) of sub-calibration tables to form the established calibration table, each sub-calibration table corresponding to one tube current of the first number ($n_1$) and second number ($n_2$) of tube currents, where $n_3=n_1+n_2$, and storing the third number ($n_3$) of sub-calibrations tables, for use in the data correction, use the acquired object scan data to generate a line-integral sinogram, based on the third number ($n_3$) of calibrations tables, and reconstruct the image of the imaging object, based on the generated line-integral sinogram.

(18) The apparatus of (17), wherein the processing circuitry is further configured to, for each fitting function of the generated plurality of fitting functions, use the fitting function to calculate a counting measurement corresponding to each tube current of the second number ($n_2$) of tube currents, wherein the first number ($n_1$) and second number ($n_2$) of tube currents are distributed across a tube current range applied during the object scan, and a tube current step among the first number ($n_1$) and second number ($n_2$) of tube currents is not larger than a predetermined threshold.

(19) A method for performing object scan data correction in an X-ray imaging system having a photon-counting detector, the X-ray imaging system including an X-ray tube for emitting X-rays, the method comprising: acquiring calibration scan data from a calibration scan performed using each slab of a plurality of slabs, with a first number ($n_1$) of tube currents applied to the X-ray tube; establishing, based on the acquired calibration scan data, the first number ($n_1$) of calibration tables to be used in data correction, each calibration table of the first number ($n_1$) of calibration tables corresponding to one tube current of the first number ($n_1$) of tube currents; calculating, for a second number ($n_2$) of tube currents, the second number ($n_2$) of calibration tables based on the first number ($n_1$) of calibration tables, where the second number ($n_2$) of tube currents are different from the first number ($n_1$) of tube currents; acquiring object scan data from an object scan performed on an imaging object; performing the data correction for the acquired object scan data, based on the first number ($n_1$) and second number ($n_2$) of calibration tables; and reconstructing an image of the imaging object based on the performed data correction.

(20) The method of (19), wherein the calculating step further comprises, for each specific tube current of the second number ($n_2$) of tube currents, selecting, from the first number ($n_1$) of calibration tables, two or more calibration tables corresponding to tube currents closest to the specific tube current, and performing interpolation on the selected two or more calibration tables to derive a calibration table for the specific tube current.

Numerous modifications and variations of the embodiments presented herein are possible in light of the above teachings. It is therefore to be understood that within the scope of the claims, the disclosure may be practiced otherwise than as specifically described herein.

The invention claimed is:

1. A method for performing object scan data correction in an X-ray imaging system having a photon-counting detector, the X-ray imaging system including an X-ray tube for emitting X-rays, the method comprising:

acquiring calibration scan data from a calibration scan performed using a plurality of slabs;

performing function fitting based on the acquired calibration scan data to generate a plurality of fitting functions corresponding to the plurality of slabs, each corresponding fitting function representing a relationship between a counting measurement detected with respect to one slab of the plurality of slabs and a tube current applied to the X-ray tube;

establishing a calibration table based on the acquired calibration scan data;

acquiring object scan data from an object scan performed on an imaging object;

performing data correction for the acquired object scan data, based on the established calibration table and the generated plurality of fitting functions; and reconstructing an image of the imaging object based on the performed data correction.

2. The method of claim 1, wherein the step of acquiring the calibration scan data further comprises acquiring the calibration scan data from the calibration scan performed using each slab of the plurality of slabs, with a first number ($n_1$) of tube currents applied to the X-ray tube, the establishing step further comprises:

establishing, based on the acquired calibration scan data, the first number ($n_1$) of sub-calibration tables to form the established calibration table, each sub-calibration table corresponding to one tube current of the first number ($n_1$) of tube currents, and storing the first number ($n_1$) of sub-calibrations tables, for use in performing the data correction, the step of performing the data correction further comprises:

for each view of the acquired object scan data, projecting a counting measurement detected by each pixel of the photon-counting detector, based on the generated plurality of fitting functions, to a projected counting measurement, as if the projected counting measurement were detected when a specific tube current of the first number ($n_1$) of tube currents is applied to the X-ray tube, and using the projected counting measurements to generate a line-integral sinogram, based on the first number ($n_1$) of sub-calibration tables, and the reconstructing step further comprises reconstructing the image of the imaging object, based on the generated line-integral sinogram.

3. The method of claim 2, wherein the X-ray imaging system further comprises a tube current detector configured to directly or indirectly detect a tube current applied to the X-ray tube during the object scan, and the projecting step further comprises:

for each view of the acquired object scan data, based on a counting measurement detected by each pixel of the photon-counting detector and a corresponding tube current detected when the view is acquired, using at least one fitting function of the generated plurality of fitted functions, to derive a corresponding fitting function with respect to an attenuation pathlength corresponding to the counting measurement, and calculating, based on the derived corresponding fitting function, a counting measurement corresponding to one tube current of the first number ($n_1$) of tube currents that is closest to the corresponding tube current detected when the view is acquired, as the projected counting measurement.

4. The method of claim 2, wherein the step of performing function fitting further comprises performing the function fitting based on the acquired calibration scan data to generate a corresponding polynomial fitting function with respect to each slab of the plurality of slabs, and a number of order of the corresponding polynomial fitting function is determined based on the first number ($n_1$).

5. The method of claim 2, wherein the step of generating the line-integral sinogram further comprises, generating a counting line-integral sinogram when the X-ray imaging system operates in a counting imaging mode, and generating a basis material line-integral sinogram when the X-ray imaging system operates in a material decomposition imaging mode, and the step of performing function fitting further comprises, when the X-ray imaging system operates in the material decomposition imaging mode, for each slab of the plurality of slabs, generating respective fitting functions specific to individual energy bins.

6. The method of claim 1, wherein the step of acquiring the calibration scan data further comprises acquiring the calibration scan data from the calibration scan performed using each slab of the plurality of slabs, where the plurality of slabs have different attenuation pathlengths from one another, and an attenuation pathlength step among the plurality of slabs is not larger than a predetermined threshold.

7. The method of claim 1, wherein the step of establishing the calibration table further comprises establishing, based on the acquired calibration scan data, a particular calibration table for calibrating a detector response of the X-ray imaging system and/or for correcting a pile-up effect of the X-ray imaging system.

8. The method of claim 1, wherein the step of acquiring the calibration scan data further comprises acquiring the calibration scan data from the calibration scan performed using each slab of the plurality of slabs, with a first number ($n_1$) of tube currents applied to the X-ray tube, the establishing step further comprises, calculating supplemental calibration data based on the generated plurality of fitting functions, as if the supplemental calibration data were acquired from a calibration scan performed on each slab of the plurality of slabs, with a second number ($n_2$) of tube currents applied to the X-ray tube, where the second number ($n_2$) of tube currents are different from the first number ($n_1$) of tube currents, establishing, based on the acquired calibration scan data and the calculated supplemental calibration data, a third number ($n_3$) of sub-calibration tables to form the established calibration table, each sub-calibration table corresponding to one tube current of the first number ($n_1$) and second number ($n_2$) of tube currents, where $n_3=n_1+n_2$, and storing the third number ($n_3$) of sub-calibrations tables, for use in the data correction, the step of performing the data correction for the acquired object scan data further comprising using the acquired object scan data to generate a line-integral sinogram, based on the third number ($n_3$) of sub-calibrations tables, and the reconstructing step further comprises reconstructing the image of the imaging object, based on the generated line-integral sinogram.

9. The method of claim 8, wherein the step of calculating the supplemental calibration data further comprises, for each fitting function of the generated plurality of fitting functions, using the fitting function to calculate a counting measurement corresponding to each tube current of the second number ($n_2$) of tube currents, the first number ($n_1$) and second number ($n_2$) of tube currents are distributed across a tube current range applied during the object scan, and a tube current step among the first number ($n_1$) and second number ($n_2$) of tube currents is not larger than a predetermined threshold.

10. An apparatus for performing object scan data correction in an X-ray imaging system having a photon-counting detector, the X-ray imaging system including an X-ray tube for emitting X-rays, the apparatus comprising:

processing circuitry configured to acquire calibration scan data from a calibration scan performed using a plurality of slabs, perform function fitting based on the acquired calibration scan data to generate a plurality of fitting functions corresponding to the plurality of slabs, each corresponding fitting function representing a relationship between a counting measurement detected with respect to one slab of the plurality of slabs and a tube current applied to the X-ray tube, establish a calibration table based on the acquired calibration scan data, acquire object scan data from an object scan performed on an imaging object, perform data correction for the acquired object scan data, based on the established calibration table and the generated plurality of fitting functions, and reconstruct an image of the imaging object based on the performed data correction.

11. The apparatus of claim 10, wherein the processing circuitry is further configured to:

acquire the calibration scan data from the calibration scan performed using each slab of the plurality of slabs, with a first number ($n_1$) of tube currents applied to the X-ray tube, establish the calibration table by, establishing, based on the acquired calibration scan data, the first number ($n_1$) of sub-calibration tables to form the established calibration table, each sub-calibration table corresponding to one tube current of the first number ($n_1$) of tube currents, and storing the first number ($n_1$) of sub-calibrations tables, for use in performing the data correction, perform the data correction by:

for each view of the acquired object scan data, projecting a counting measurement detected by each pixel of the photon-counting detector, based on the generated plurality of fitting functions, to a projected counting measurement, as if the projected counting measurement were detected when a specific tube current of the first number ($n_1$) of tube currents is applied to the X-ray tube, and using the projected counting measurements to generate a line-integral sinogram, based on the first number ($n_1$) of sub-calibration tables, and reconstruct the image of the imaging object, based on the generated line-integral sinogram.

12. The apparatus of claim 11, wherein the X-ray imaging system further comprises a tube current detector configured to directly or indirectly detect a tube current applied to the X-ray tube during the object scan, and the processing circuitry is further configured to:

for each view of the acquired object scan data, based on a counting measurement detected by each pixel of the photon-counting detector and a corresponding tube current detected when the view is acquired, use at least one fitting function of the generated plurality of fitted functions, to derive a corresponding fitting function with respect to an attenuation pathlength corresponding to the counting measurement, and calculate, based on the derived corresponding fitting function, a counting measurement corresponding to one tube current of the first number ($n_1$) of tube currents that is closest to the corresponding tube current detected when the view is acquired, as the projected counting measurement.

13. The apparatus of claim 11, wherein the processing circuitry is further configured to perform the function fitting based on the acquired calibration scan data to generate a corresponding polynomial fitting function for each slab of the plurality of slabs, and a number of order of the corresponding polynomial fitting function is determined based on the first number ($n_1$).

14. The apparatus of claim 11, wherein the processing circuitry is further configured to:

generate a counting line-integral sinogram when the X-ray imaging system operates in a counting imaging mode, and generate a basis material line-integral sinogram when the X-ray imaging system operates in a material decomposition imaging mode, and when the X-ray imaging system operates in the material decomposition imaging mode, for each slab of the plurality of slabs, generate respective fitting functions specific to individual energy bins.

15. The apparatus of claim 10, wherein the processing circuitry is further configured to acquire the calibration scan data from the calibration scan performed using each slab of the plurality of slabs, where the plurality of slabs have different attenuation pathlengths from one another, and an attenuation pathlength step among the plurality of slabs is not larger than a predetermined threshold.

16. The apparatus of claim 10, wherein the processing circuitry is further configured to establish, based on the acquired calibration scan data, a particular calibration table for calibrating a detector response of the X-ray imaging system and/or for correcting a pile-up effect of the X-ray imaging system.

17. The apparatus of claim 10, wherein the processing circuitry is further configured to:

acquire the calibration scan data from the calibration scan performed using each slab of the plurality of slabs, with a first number ($n_1$) of tube currents applied to the X-ray tube, establish the calibration table by calculating supplemental calibration data based on the generated plurality of fitting functions, as if the supplemental calibration data were acquired from a calibration scan performed on each slab of the plurality of slabs, with a second number ($n_2$) of tube currents applied to the X-ray tube, where the second number ($n_2$) of tube currents are different from the first number ($n_1$) of tube currents, establishing, based on the acquired calibration scan data and the calculated supplemental calibration data, a third number ($n_3$) of sub-calibration tables to form the established calibration table, each sub-calibration table corresponding to one tube current of the first number ($n_1$) and second number ($n_2$) of tube currents, where $n_3=n_1+n_2$, and storing the third number ($n_3$) of sub-calibrations tables, for use in the data correction, use the acquired object scan data to generate a line-integral sinogram, based on the third number ($n_3$) of calibrations tables, and reconstruct the image of the imaging object, based on the generated line-integral sinogram.

18. The apparatus of claim 17, wherein the processing circuitry is further configured to, for each fitting function of the generated plurality of fitting functions, use the fitting function to calculate a counting measurement corresponding to each tube current of the second number ($n_2$) of tube currents, wherein the first number ($n_1$) and second number ($n_2$) of tube currents are distributed across a tube current range applied during the object scan, and a tube current step among the first number ($n_1$) and second number ($n_2$) of tube currents is not larger than a predetermined threshold.

19. A method for performing object scan data correction in an X-ray imaging system having a photon-counting detector, the X-ray imaging system including an X-ray tube for emitting X-rays, the method comprising:

acquiring calibration scan data from a calibration scan performed using each slab of a plurality of slabs, with a first number ($n_1$) of tube currents applied to the X-ray tube;

establishing, based on the acquired calibration scan data, the first number ($n_1$) of calibration tables to be used in data correction, each calibration table of the first number ($n_1$) of calibration tables corresponding to one tube current of the first number ($n_1$) of tube currents;

calculating, for a second number ($n_2$) of tube currents, the second number ($n_2$) of calibration tables based on the first number ($n_1$) of calibration tables, where the second number ($n_2$) of tube currents are different from the first number ($n_1$) of tube currents;

acquiring object scan data from an object scan performed on an imaging object;

performing the data correction for the acquired object scan data, based on the first number ($n_1$) and second number ($n_2$) of calibration tables; and reconstructing an image of the imaging object based on the performed data correction.

20. The method of claim 19, wherein the calculating step further comprises, for each specific tube current of the second number ($n_2$) of tube currents, selecting, from the first number ($n_1$) of calibration tables, two or more calibration tables corresponding to tube currents closest to the specific tube current, and performing interpolation on the selected two or more calibration tables to derive a calibration table for the specific tube current.

* * * * *